(12) United States Patent
Morton

(10) Patent No.: US 8,135,110 B2
(45) Date of Patent: Mar. 13, 2012

(54) X-RAY TOMOGRAPHY INSPECTION SYSTEMS

(75) Inventor: Edward James Morton, Surrey (GB)

(73) Assignee: Rapiscan Systems, Inc., Hawthorne, CA (US)

( * ) Notice: Subject to any disclaimer, the term of this patent is extended or adjusted under 35 U.S.C. 154(b) by 0 days.

(21) Appl. No.: 12/142,005

(22) Filed: Jun. 19, 2008

(65) Prior Publication Data

US 2009/0060135 A1 Mar. 5, 2009

Related U.S. Application Data

(63) Continuation of application No. 12/097,422, filed on Jun. 13, 2008, now Pat. No. 7,876,879.

(30) Foreign Application Priority Data

Dec. 16, 2005 (GB) .................................. 0525593.0

(51) Int. Cl.
*G01N 23/04* (2006.01)
*G01N 23/203* (2006.01)

(52) U.S. Cl. .................... 378/57; 378/6; 378/10; 378/87

(58) Field of Classification Search ................ 378/6, 10, 378/57, 87
See application file for complete search history.

(56) References Cited

U.S. PATENT DOCUMENTS

| | | |
|---|---|---|
| 2,952,790 A | 9/1960 | Steen |
| 3,239,706 A | 3/1966 | Farrell et al. |
| 3,768,645 A | 10/1973 | Conway et al. |
| 4,057,725 A | 11/1977 | Wagner |
| 4,105,922 A | 8/1978 | Lambert et al. |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura et al. |
| 4,340,816 A | 7/1982 | Schott |
| 4,352,021 A | 9/1982 | Boyd et al. |
| 4,375,695 A * | 3/1983 | Harding et al. .................... 378/6 |
| 4,384,209 A * | 5/1983 | Wagner et al. .................... 378/14 |
| 4,468,802 A | 8/1984 | Friedel |
| 4,672,649 A | 6/1987 | Rutt |
| 4,675,890 A | 6/1987 | Plessis et al. |
| RE32,961 E | 6/1989 | Wagner |

(Continued)

FOREIGN PATENT DOCUMENTS

AU 2003254124 A1 2/2004

(Continued)

OTHER PUBLICATIONS

PCT International Search Report (PCT/GB2006/004684), Feb. 23, 2007, CXR Ltd.

(Continued)

*Primary Examiner* — Edward Glick
*Assistant Examiner* — Thomas R Artman
(74) *Attorney, Agent, or Firm* — Novel IP

(57) ABSTRACT

The present invention is an X-ray scanning system with an X-ray source arranged to generate X-rays from X-ray source positions around a scanning region, a first set of detectors arranged to detect X-rays transmitted through the scanning region, a second set of detectors arranged to detect X-rays scattered within the scanning region, and a processor arranged to process outputs from the detectors to generate image data.

16 Claims, 12 Drawing Sheets

U.S. PATENT DOCUMENTS

| | | |
|---|---|---|
| 4,866,745 A | 9/1989 | Akai |
| 4,868,856 A | 9/1989 | Frith et al. |
| 4,887,604 A | 12/1989 | Shefer et al. |
| 4,987,584 A | 1/1991 | Doenges |
| 5,033,106 A | 7/1991 | Kita |
| 5,144,191 A | 9/1992 | Jones et al. |
| 5,182,764 A | 1/1993 | Peschmann et al. |
| 5,247,556 A | 9/1993 | Eckert et al. |
| 5,247,561 A * | 9/1993 | Kotowski ................... 378/87 |
| 5,259,014 A | 11/1993 | Brettschneider |
| 5,272,627 A | 12/1993 | Maschhoff et al. |
| 5,313,511 A | 5/1994 | Annis et al. |
| 5,319,547 A | 6/1994 | Krug et al. |
| 5,367,552 A | 11/1994 | Peschmann |
| 5,410,156 A | 4/1995 | Miller |
| 5,412,702 A | 5/1995 | Sata |
| 5,467,377 A | 11/1995 | Dawson |
| 5,490,196 A | 2/1996 | Rudich et al. |
| 5,490,218 A | 2/1996 | Krug et al. |
| 5,511,104 A | 4/1996 | Mueller et al. |
| 5,557,108 A | 9/1996 | Tumer |
| 5,570,403 A | 10/1996 | Yamazaki et al. |
| 5,600,700 A * | 2/1997 | Krug et al. ................ 378/57 |
| 5,604,778 A | 2/1997 | Polacin et al. |
| 5,606,167 A | 2/1997 | Miller |
| 5,633,907 A | 5/1997 | Gravelle et al. |
| 5,642,393 A | 6/1997 | Krug et al. |
| 5,661,774 A | 8/1997 | Gordon et al. |
| 5,689,541 A | 11/1997 | Schardt |
| 5,712,926 A | 1/1998 | Eberhard et al. |
| 5,796,802 A | 8/1998 | Gordon |
| 5,818,897 A | 10/1998 | Gordon |
| 5,838,758 A | 11/1998 | Krug et al. |
| 5,841,831 A | 11/1998 | Hell et al. |
| 5,859,891 A | 1/1999 | Hibbard |
| 5,881,122 A | 3/1999 | Crawford et al. |
| 5,887,047 A | 3/1999 | Bailey et al. |
| 5,901,198 A | 5/1999 | Crawford et al. |
| 5,905,806 A | 5/1999 | Eberhard et al. |
| 5,909,477 A | 6/1999 | Crawford et al. |
| 5,910,973 A | 6/1999 | Grodzins |
| 5,930,326 A | 7/1999 | Rothschild et al. |
| 5,966,422 A | 10/1999 | Dafni et al. |
| 5,974,111 A | 10/1999 | Krug et al. |
| 5,982,843 A | 11/1999 | Bailey et al. |
| 5,987,097 A | 11/1999 | Salasoo |
| 6,018,562 A * | 1/2000 | Willson ..................... 378/9 |
| 6,021,174 A | 2/2000 | Campbell |
| 6,026,143 A | 2/2000 | Simanovsky et al. |
| 6,026,171 A | 2/2000 | Hiraoglu et al. |
| 6,035,014 A | 3/2000 | Hiraoglu et al. |
| 6,037,597 A | 3/2000 | Karavolos |
| 6,067,366 A | 5/2000 | Simanovsky et al. |
| 6,075,871 A | 6/2000 | Simanovsky et al. |
| 6,076,400 A | 6/2000 | Bechwati et al. |
| 6,078,642 A | 6/2000 | Simanovsky et al. |
| 6,081,580 A * | 6/2000 | Grodzins et al. .......... 378/87 |
| 6,088,423 A * | 7/2000 | Krug et al. ................ 378/57 |
| 6,091,795 A | 7/2000 | Schafer |
| 6,108,396 A | 8/2000 | Bechwati et al. |
| 6,111,974 A | 8/2000 | Hiraoglu et al. |
| 6,118,852 A | 9/2000 | Rogers et al. |
| 6,122,343 A | 9/2000 | Pidcock |
| 6,128,365 A | 10/2000 | Bechwati et al. |
| 6,149,592 A | 11/2000 | Yanof et al. |
| 6,163,591 A | 12/2000 | Benjamin |
| 6,181,765 B1 | 1/2001 | Sribar et al. |
| 6,183,139 B1 | 2/2001 | Solomon et al. |
| 6,185,272 B1 | 2/2001 | Hiraoglu et al. |
| 6,188,745 B1 | 2/2001 | Gordon |
| 6,195,444 B1 | 2/2001 | Simanovsky et al. |
| 6,216,540 B1 | 4/2001 | Nelson et al. |
| 6,218,943 B1 | 4/2001 | Ellenbogen |
| 6,236,709 B1 | 5/2001 | Perry et al. |
| 6,252,929 B1 | 6/2001 | Swift et al. |
| 6,256,404 B1 | 7/2001 | Gordon et al. |
| 6,269,142 B1 | 7/2001 | Smith |
| 6,272,230 B1 | 8/2001 | Hiraoglu et al. |
| 6,278,115 B1 * | 8/2001 | Annis et al. ............. 250/363.01 |
| 6,292,533 B1 | 9/2001 | Swift et al. |
| 6,304,629 B1 | 10/2001 | Conway et al. |
| 6,317,509 B1 | 11/2001 | Simanovsky et al. |
| 6,324,249 B1 | 11/2001 | Fazzio |
| 6,345,113 B1 | 2/2002 | Crawford et al. |
| 6,418,189 B1 | 7/2002 | Schafer |
| 6,429,578 B1 | 8/2002 | Danielsson et al. |
| 6,430,255 B2 | 8/2002 | Fenkart et al. |
| 6,445,765 B1 | 9/2002 | Frank et al. |
| 6,459,755 B1 | 10/2002 | Li |
| 6,459,761 B1 | 10/2002 | Grodzins et al. |
| 6,459,764 B1 | 10/2002 | Chalmers et al. |
| 6,507,025 B1 | 1/2003 | Verbinski et al. |
| 6,546,072 B1 | 4/2003 | Chalmers |
| 6,556,653 B2 * | 4/2003 | Hussein ..................... 378/90 |
| 6,563,906 B2 | 5/2003 | Hussein et al. |
| 6,590,956 B2 | 7/2003 | Fenkart et al. |
| 6,618,466 B1 | 9/2003 | Ning |
| 6,647,091 B2 | 11/2003 | Fenkart et al. |
| 6,647,094 B2 | 11/2003 | Harding et al. |
| 6,647,095 B2 | 11/2003 | Hsieh |
| 6,687,333 B2 | 2/2004 | Carroll et al. |
| 6,690,766 B2 | 2/2004 | Kresse |
| 6,707,879 B2 | 3/2004 | McClelland et al. |
| 6,715,533 B2 | 4/2004 | Kresse |
| 6,721,387 B1 | 4/2004 | Naidu et al. |
| 6,735,271 B1 | 5/2004 | Rand et al. |
| 6,737,652 B2 | 5/2004 | Lanza et al. |
| 6,748,043 B1 | 6/2004 | Dobbs |
| 6,754,298 B2 | 6/2004 | Fessler |
| 6,760,407 B2 | 7/2004 | Price et al. |
| 6,770,884 B2 | 8/2004 | Bryman |
| 6,775,348 B2 | 8/2004 | Hoffman |
| 6,788,761 B2 | 9/2004 | Bijjani et al. |
| 6,813,374 B1 | 11/2004 | Karimi et al. |
| 6,816,571 B2 | 11/2004 | Bijjani et al. |
| 6,827,265 B2 | 12/2004 | Knowles et al. |
| 6,830,185 B2 | 12/2004 | Tsikos et al. |
| 6,837,432 B2 | 1/2005 | Tsikos et al. |
| 6,856,667 B2 | 2/2005 | Ellengogen |
| 6,859,514 B2 | 2/2005 | Hoffman |
| 6,901,135 B2 | 5/2005 | Fox et al. |
| 6,906,329 B2 | 6/2005 | Bryman |
| 6,907,101 B2 | 6/2005 | Hoffman |
| 6,922,455 B2 | 7/2005 | Jurczyk et al. |
| 6,922,460 B2 | 7/2005 | Skatter et al. |
| 6,922,461 B2 | 7/2005 | Kang et al. |
| 6,933,504 B2 | 8/2005 | Hoffman et al. |
| 6,934,354 B2 | 8/2005 | Hoffman |
| 6,940,071 B2 | 9/2005 | Ramsden et al. |
| 6,944,264 B2 | 9/2005 | Bijjani et al. |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey et al. |
| 6,953,935 B1 | 10/2005 | Hoffman |
| 6,957,913 B2 | 10/2005 | Renkart et al. |
| 6,962,289 B2 | 11/2005 | Vatan et al. |
| 6,968,030 B2 | 11/2005 | Hoffman |
| 6,968,034 B2 | 11/2005 | Ellengogen |
| 6,971,577 B2 | 12/2005 | Tsikos et al. |
| 6,973,158 B2 | 12/2005 | Besson |
| 6,975,698 B2 | 12/2005 | Katcha et al. |
| 6,978,936 B2 | 12/2005 | Tsikos et al. |
| 6,980,627 B2 | 12/2005 | Qiu et al. |
| 6,990,171 B2 | 1/2006 | Toth et al. |
| 6,990,172 B2 | 1/2006 | Toth et al. |
| 6,991,371 B2 | 1/2006 | Georgeson et al. |
| 6,993,115 B2 | 1/2006 | McGuire et al. |
| 6,996,209 B2 | 2/2006 | Marek |
| 7,010,083 B2 | 3/2006 | Hoffman |
| 7,016,459 B2 | 3/2006 | Ellenbogen et al. |
| 7,020,241 B2 | 3/2006 | Beneke et al. |
| 7,020,242 B2 | 3/2006 | Ellengogen |
| 7,023,956 B2 | 4/2006 | Heaton et al. |
| 7,023,957 B2 | 4/2006 | Bijjani et al. |
| 7,027,553 B2 | 4/2006 | Dunham et al. |
| 7,027,554 B2 | 4/2006 | Gaultier et al. |

| | | |
|---|---|---|
| 7,031,430 B2 | 4/2006 | Kaucic, Jr. et al. |
| 7,031,434 B1 | 4/2006 | Saunders et al. |
| 7,034,313 B2 | 4/2006 | Hoffman |
| 7,039,154 B1 | 5/2006 | Ellenbogen et al. |
| 7,045,787 B1 | 5/2006 | Verbinski et al. |
| 7,046,756 B2 | 5/2006 | Hoffman |
| 7,046,761 B2 | 5/2006 | Ellenbogen et al. |
| 7,050,536 B1 | 5/2006 | Fenkart et al. |
| 7,054,408 B2 | 5/2006 | Jiang et al. |
| 7,062,009 B2 | 6/2006 | Karimi et al. |
| 7,062,011 B1 | 6/2006 | Tybinkowski et al. |
| 7,062,074 B1 | 6/2006 | Beneke |
| 7,064,334 B2 | 6/2006 | Hoffman et al. |
| 7,065,175 B2 | 6/2006 | Green |
| 7,065,179 B2 | 6/2006 | Block et al. |
| 7,068,749 B2 | 6/2006 | Kollegal et al. |
| 7,068,750 B2 | 6/2006 | Toth et al. |
| 7,068,751 B2 | 6/2006 | Toth et al. |
| 7,072,434 B1 | 7/2006 | Tybinkowski et al. |
| 7,076,029 B2 | 7/2006 | Toth et al. |
| 7,078,699 B2 | 7/2006 | Seppi |
| 7,081,628 B2 | 7/2006 | Granfors et al. |
| 7,084,404 B2 | 8/2006 | Hoffman et al. |
| 7,087,902 B2 | 8/2006 | Wang et al. |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,103,137 B2 | 9/2006 | Seppi et al. |
| 7,110,488 B2 | 9/2006 | Katcha et al. |
| 7,112,797 B2 | 9/2006 | Hoge |
| 7,116,749 B2 | 10/2006 | Besson |
| 7,116,751 B2 | 10/2006 | Ellenbogen et al. |
| 7,119,553 B2 | 10/2006 | Yang et al. |
| 7,123,681 B2 | 10/2006 | Ellenbogen et al. |
| 7,127,027 B2 | 10/2006 | Hoffman |
| 7,130,374 B1 | 10/2006 | Jacobs et al. |
| 7,133,491 B2 | 11/2006 | Bernardi et al. |
| 7,136,450 B2 | 11/2006 | Ying et al. |
| 7,136,451 B2 | 11/2006 | Naidu et al. |
| 7,139,367 B1 | 11/2006 | Le |
| 7,139,406 B2 | 11/2006 | McClelland et al. |
| 7,142,629 B2 | 11/2006 | Edic et al. |
| 7,149,278 B2 | 12/2006 | Arenson et al. |
| 7,149,339 B2 | 12/2006 | Veneruso |
| 7,155,812 B1 | 1/2007 | Peterson et al. |
| 7,158,611 B2 | 1/2007 | Heismann et al. |
| 7,164,747 B2 | 1/2007 | Ellenbogen et al. |
| 7,164,750 B2 | 1/2007 | Nabors et al. |
| 7,166,458 B2 | 1/2007 | Ballerstadt et al. |
| 7,167,539 B1 | 1/2007 | Hoffman |
| 7,173,998 B2 | 2/2007 | Hoffman et al. |
| 7,177,387 B2 | 2/2007 | Yasunaga et al. |
| 7,177,391 B2 | 2/2007 | Chapin et al. |
| 7,190,757 B2 | 3/2007 | Ying et al. |
| 7,192,031 B2 | 3/2007 | Dunham et al. |
| 7,197,113 B1 | 3/2007 | Katcha et al. |
| 7,197,172 B1 | 3/2007 | Naidu et al. |
| 7,203,629 B2 | 4/2007 | Ozis et al. |
| 7,206,379 B2 | 4/2007 | Lemaitre |
| 7,215,731 B1 | 5/2007 | Basu et al. |
| 7,215,738 B2 | 5/2007 | Muenchau et al. |
| 7,218,700 B2 | 5/2007 | Huber et al. |
| 7,218,704 B1 | 5/2007 | Adams et al. |
| 7,224,763 B2 | 5/2007 | Naidu et al. |
| 7,224,765 B2 | 5/2007 | Ellenbogen |
| 7,224,766 B2 | 5/2007 | Jiang et al. |
| 7,224,769 B2 | 5/2007 | Turner |
| 7,233,640 B2 | 6/2007 | Ikhlef et al. |
| 7,236,564 B2 | 6/2007 | Hopkins et al. |
| 7,238,945 B2 | 7/2007 | Hoffman et al. |
| 7,247,856 B2 | 7/2007 | Hoge |
| 7,251,310 B2 | 7/2007 | Smith |
| 7,260,170 B2 | 8/2007 | Arenson et al. |
| 7,260,171 B1 | 8/2007 | Arenson et al. |
| 7,260,172 B2 | 8/2007 | Arenson et al. |
| 7,260,173 B2 | 8/2007 | Wakayama et al. |
| 7,260,174 B2 | 8/2007 | Hoffman et al. |
| 7,260,182 B2 | 8/2007 | Toth et al. |
| 7,263,160 B2 | 8/2007 | Schlomka et al. |
| 7,266,180 B1 | 9/2007 | Saunders et al. |
| 7,272,429 B2 | 9/2007 | Walker et al. |
| 7,274,767 B2 | 9/2007 | Clayton et al. |
| 7,277,577 B2 | 10/2007 | Ying et al. |
| 7,279,120 B2 | 10/2007 | Cheng et al. |
| 7,280,631 B2 | 10/2007 | De Man et al. |
| 7,282,727 B2 | 10/2007 | Retsky |
| 7,283,604 B2 | 10/2007 | De Man et al. |
| 7,283,609 B2 | 10/2007 | Possin et al. |
| 7,295,019 B2 | 11/2007 | Yang et al. |
| 7,295,651 B2 | 11/2007 | Delgado et al. |
| 7,298,812 B2 | 11/2007 | Tkaczyk et al. |
| 7,302,083 B2 | 11/2007 | Larson et al. |
| 7,308,073 B2 | 12/2007 | Tkaczyk et al. |
| 7,308,074 B2 | 12/2007 | Jiang et al. |
| 7,308,077 B2 | 12/2007 | Bijjani et al. |
| 7,317,195 B2 | 1/2008 | Eikman |
| 7,317,390 B2 | 1/2008 | Huey et al. |
| 7,319,737 B2 | 1/2008 | Singh |
| 7,324,625 B2 | 1/2008 | Eilbert |
| 7,327,853 B2 | 2/2008 | Ying et al. |
| 7,330,527 B2 | 2/2008 | Hoffman et al. |
| 7,330,535 B2 | 2/2008 | Arenson et al. |
| 7,333,587 B2 | 2/2008 | De Man et al. |
| 7,333,588 B2 | 2/2008 | Mistretta et al. |
| 7,333,589 B2 | 2/2008 | Ellenbogen et al. |
| 7,335,887 B1 | 2/2008 | Verbinski et al. |
| 7,336,769 B2 | 2/2008 | Arenson et al. |
| 7,349,525 B2 | 3/2008 | Morton et al. |
| 7,369,640 B2 | 5/2008 | Seppi et al. |
| 7,400,701 B1 * | 7/2008 | Cason ............... 378/57 |
| 7,440,543 B2 | 10/2008 | Morton |
| 7,486,760 B2 * | 2/2009 | Harding ............. 378/7 |
| 7,486,769 B2 * | 2/2009 | Brondo, Jr. ......... 378/57 |
| 7,492,855 B2 | 2/2009 | Hopkins et al. |
| 7,512,215 B2 | 3/2009 | Morton et al. |
| 7,564,939 B2 | 7/2009 | Morton et al. |
| 7,590,215 B2 * | 9/2009 | Schlomka ............ 378/4 |
| 7,593,506 B2 * | 9/2009 | Cason ............... 378/90 |
| 7,684,538 B2 | 3/2010 | Morton |
| 2001/0022346 A1 | 9/2001 | Katagami et al. |
| 2001/0033635 A1 | 10/2001 | Kuwabara |
| 2002/0031202 A1 | 3/2002 | Callerame et al. |
| 2002/0094064 A1 | 7/2002 | Zhou et al. |
| 2002/0176531 A1 | 11/2002 | McClelland et al. |
| 2003/0021377 A1 | 1/2003 | Turner et al. |
| 2003/0053597 A1 | 3/2003 | Flohr et al. |
| 2004/0017888 A1 | 1/2004 | Seppi et al. |
| 2004/0120454 A1 | 6/2004 | Ellenbogen et al. |
| 2004/0213378 A1 | 10/2004 | Zhou et al. |
| 2004/0213379 A1 | 10/2004 | Bittl |
| 2004/0252807 A1 | 12/2004 | Skatter et al. |
| 2004/0258305 A1 | 12/2004 | Burnham et al. |
| 2005/0031075 A1 | 2/2005 | Hopkins et al. |
| 2005/0053189 A1 | 3/2005 | Gohno et al. |
| 2005/0105682 A1 | 5/2005 | Heumann et al. |
| 2005/0111610 A1 * | 5/2005 | De Man et al. .......... 378/10 |
| 2005/0157925 A1 | 7/2005 | Lorenz |
| 2005/0169422 A1 | 8/2005 | Ellenbogen |
| 2005/0169423 A1 | 8/2005 | Ellenbogen et al. |
| 2005/0190882 A1 | 9/2005 | McGuire |
| 2005/0226364 A1 | 10/2005 | De Man et al. |
| 2005/0281390 A1 | 12/2005 | Johnson et al. |
| 2006/0018428 A1 | 1/2006 | Li et al. |
| 2006/0113163 A1 | 6/2006 | Hu et al. |
| 2006/0273259 A1 | 12/2006 | Li et al. |
| 2007/0003003 A1 | 1/2007 | Seppi et al. |
| 2007/0053495 A1 | 3/2007 | Morton et al. |
| 2007/0096030 A1 | 5/2007 | Li et al. |
| 2007/0110215 A1 | 5/2007 | Hu et al. |
| 2007/0133740 A1 | 6/2007 | Kang et al. |
| 2007/0172024 A1 | 7/2007 | Morton et al. |
| 2007/0183568 A1 | 8/2007 | Kang et al. |
| 2007/0263767 A1 * | 11/2007 | Brondo ............... 378/57 |
| 2008/0056432 A1 | 3/2008 | Pack et al. |
| 2008/0056435 A1 | 3/2008 | Basu et al. |
| 2009/0161816 A1 | 6/2009 | De Man et al. |

FOREIGN PATENT DOCUMENTS

| | | |
|---|---|---|
| CN | 1626039 A | 6/2005 |
| CN | 1795527 A | 6/2006 |
| DE | 2729353 | 1/1979 |
| DE | 102004056590 A1 | 6/2005 |
| EP | 0 432 568 | 6/1991 |
| EP | 0 531 993 | 3/1993 |
| EP | 0 584 871 | 3/1994 |
| EP | 0873511 A1 | 10/1998 |
| EP | 0 924 742 | 6/1999 |
| EP | 0 930 046 | 7/1999 |
| EP | 1 277 439 | 1/2003 |
| EP | 1374776 | 1/2004 |
| EP | 1540318 A1 | 6/2005 |
| EP | 1618584 A2 | 1/2006 |
| EP | 1689640 A2 | 8/2006 |
| FR | 2328280 | 5/1977 |
| GB | 1497396 | 1/1978 |
| GB | 1526041 | 9/1978 |
| GB | 2 015 245 | 9/1979 |
| GB | 2089109 | 6/1982 |
| GB | 2 212 903 | 8/1989 |
| GB | 2418529 A | 3/2006 |
| GB | 2437777 | 11/2007 |
| JP | 570175247 | 10/1982 |
| JP | 590016254 | 1/1984 |
| JP | 59075549 | 4/1984 |
| JP | 60 0015546 | 1/1985 |
| JP | 60 0021440 | 2/1985 |
| JP | 04 079128 | 3/1992 |
| JP | 2004 079128 | 3/1992 |
| JP | 060038957 | 2/1994 |
| JP | 10 211196 | 8/1998 |
| JP | 2001 176408 | 6/2001 |
| JP | 2003126075 | 5/2003 |
| JP | 2004000605 | 1/2004 |
| JP | 2005013768 | 1/2005 |
| JP | 2005177469 A | 7/2005 |
| NL | 1027596 C2 | 11/2005 |
| WO | WO92/17771 | 3/1992 |
| WO | WO 95/28715 | 10/1995 |
| WO | WO 97/18462 A | 5/1997 |
| WO | WO 99/60387 | 11/1999 |
| WO | WO0231857 | 4/2002 |
| WO | WO 03/051201 | 6/2003 |
| WO | WO 03/105159 | 12/2003 |
| WO | WO 2004/010127 A | 1/2004 |
| WO | WO 2004/037088 | 5/2004 |
| WO | WO 2004/097889 A2 | 11/2004 |
| WO | WO 2004/111625 | 12/2004 |
| WO | WO 2005/017566 A2 | 2/2005 |
| WO | WO 2005/050405 A2 | 6/2005 |
| WO | WO 2005/084351 | 9/2005 |
| WO | WO2006047718 | 5/2006 |
| WO | WO 2006/135586 | 12/2006 |
| WO | WO 2007/076707 | 7/2007 |
| WO | WO 2007/079675 | 7/2007 |

OTHER PUBLICATIONS

PCT Search Report, Aug. 10, 2004, Morton, Edward James et al Search Report PCT/GB2004/001747.

Combined Search and Examination Report for GB1017187.4, Jun. 21, 2007, CXR Limited.

US 5,987,079, 11/1999, Scott et al. (withdrawn)

* cited by examiner

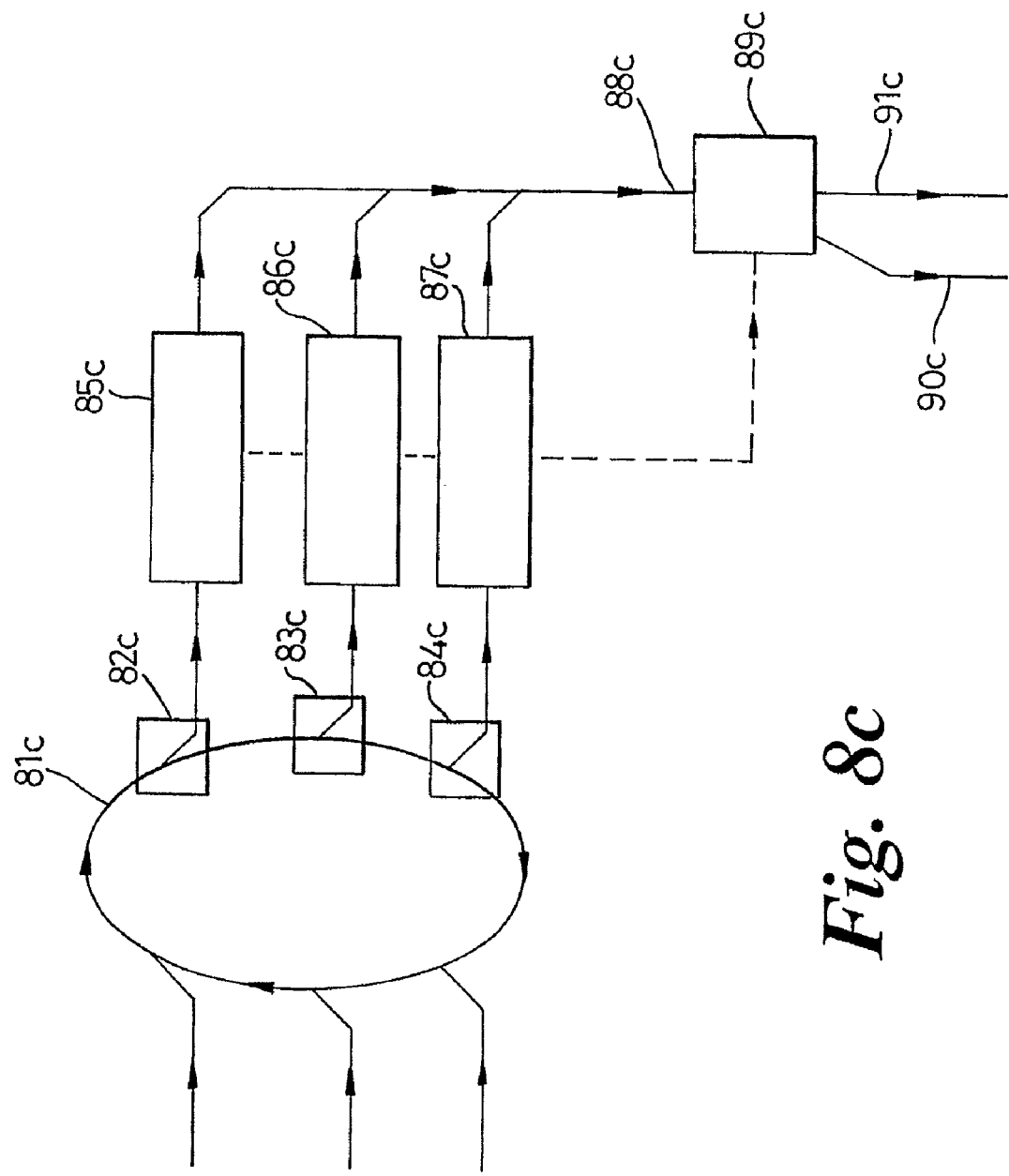

US 8,135,110 B2

X-RAY TOMOGRAPHY INSPECTION SYSTEMS

CROSS-REFERENCE TO RELATED APPLICATIONS

The present application is a continuation of U.S. patent application Ser. No. 12/097,422, entitled "X-Ray Tomography Inspection Systems", and filed on Jun. 13, 2008, which is a National Stage application of PCT/GB2006/004684, filed on Dec. 15, 2006, which further claims priority from Great Britain Patent Application Number 0525593.0, filed on Dec. 16, 2005.

BACKGROUND OF THE INVENTION

The present invention relates to X-ray scanning. In has particular application in security screening of baggage, packages and other suspicious objects although it could equally be used in other suitable applications.

X-ray computed tomography (CT) scanners have been used in security screening in airports for several years. A conventional system comprises an X-ray tube that is rotated about an axis with an arcuate X-ray detector also rotated at the same speed around the same axis. The conveyor belt on which the baggage is carried is placed within a suitable aperture around the central axis of rotation, and moved along the axis as the tube is rotated. A fan-beam of X-radiation passes from the source through the object to be inspected to the X-ray detector array.

The X-ray detector array records the intensity of X-rays passed through the object to be inspected at several locations along its length. One set of projection data is recorded at each of a number of source angles. From these recorded X-ray intensities, it is possible to form a tomographic (cross-sectional) image, typically by means of a filtered back projection algorithm. In order to produce an accurate tomographic image of an object, such as a bag or package, it can be shown that there is a requirement that the X-ray source pass through every plane through the object. In the arrangement described above, this is achieved by the rotational scanning of the X-ray source, and the longitudinal motion of the conveyor on which the object is carried.

In this type of system the rate at which X-ray tomographic scans can be collected is dependent on the speed of rotation of the gantry that holds the X-ray source and detector array. In a modern CT gantry, the entire tube-detector assembly and gantry will complete two to four revolutions per second. This allows up to four or eight tomographic scans to be collected per second respectively.

As the state-of-the-art has developed, the single ring of X-ray detectors has been replaced by multiple rings of detectors. This allows many slices (typically 8) to be scanned simultaneously and reconstructed using filtered back projection methods adapted from the single scan machines. With a continuous movement of the conveyor through the imaging system, the source describes a helical scanning motion about the object. This allows a more sophisticated cone-beam image reconstruction method to be applied that can in principle offer a more accurate volume image reconstruction.

In a further development, swept electron beam scanners have been demonstrated in medical applications whereby the mechanical scanning motion of the X-ray source and detectors is eliminated, being replaced by a continuous ring (or rings) of X-ray detectors that surround the object under inspection with a moving X-ray source being generated as a result of sweeping an electron beam around an arcuate anode. This allows images to be obtained more rapidly than in conventional scanners. However, because the electron source lies on the axis of rotation, such swept beam scanners are not compatible with conveyor systems which themselves pass close, and parallel, to the axis of rotation.

SUMMARY OF THE INVENTION

The present invention provides an X-ray scanning system for inspecting items, the system comprising an X-ray source extending around a scanning volume, and defining a plurality of source points from which X-rays can be directed through the scanning volume, an X-ray detector array also extending around the scanning volume and arranged to detect X-rays from the source points which have passed through the scanning volume and produce output signals dependent on the detected X-rays, and a conveyor arranged to convey the items through the scanning volume.

The present invention further provides a networked inspection system comprising an X-ray scanning system, a workstation and connection means arranged to connect the scanning system to the workstation, the scanning system comprising an X-ray source extending around a scanning volume, and defining a plurality of source points from which X-rays can be directed through the scanning volume, an X-ray detector array also extending around the scanning volume and arranged to detect X-rays from the source points which have passed through the scanning volume and produce output signals dependent on the detected X-rays, and a conveyor arranged to convey the items through the scanning volume.

The present invention further provides a sorting system for sorting items, the system comprising a tomographic scanner arranged to scan a plurality of scanning regions of each item thereby to produce a scanner output, analysing means arranged to analyse the scanner output and allocate each item to one of a plurality of categories at least partly on the basis of the scanner output, and sorting means arranged to sort items at least partly on the basis of the categories to which they have been allocated.

The present invention further provides an X-ray scanning system comprising an X-ray source arranged to generate X-rays from a plurality of X-ray source positions around a scanning region, a first set of detectors arranged to detect X-rays transmitted through the scanning region, a second set of detectors arranged to detect X-rays scattered within the scanning region, and processing means arranged to process outputs from the first set of detectors to generate image data which defines an image of the scanning region, to analyse the image data to identify an object within the image, and to process the outputs from the second set of detectors to generate scattering data, and to associate parts of the scattering data with the object.

The present invention further provides a data collecting system for collecting data from an X-ray scanner, the system comprising a memory having a plurality of areas each being associated with a respective area of an image, data input means arranged to receive input data from a plurality of X-ray detectors in a predetermined sequence, processing means arranged to generate from the input data X-ray transmission data and X-ray scattering data associated with each of the areas of the image, and to store the X-ray transmission data and the X-ray scattering data in the appropriate memory areas.

The present invention further provides an X-ray scanning system comprising a scanner arranged to scan an object to generate scanning data defining a tomographic X-ray image of the object, and processing means arranged to analyse the scanning data to extract at least one parameter of the image data and to allocate the object to one of a plurality of categories on the basis of the at least one parameter.

BRIEF DESCRIPTION OF THE DRAWINGS

Preferred embodiments of the present invention will now be described by way of example only with reference to the accompanying drawings in which:

FIGS. 8a, 8b and 8c are schematic diagrams of baggage sorting systems according to further embodiments of the invention;

DETAILED DESCRIPTION OF THE DRAWINGS

Figure 1:
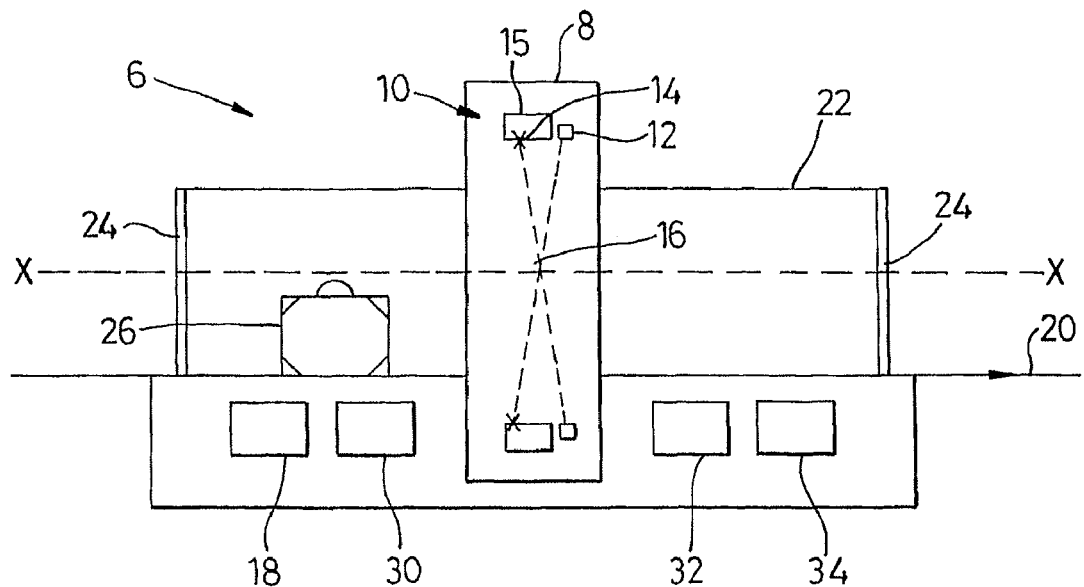
FIG. 1 is a longitudinal section of a real time tomography security scanning system according to a first embodiment of the invention.
Figure 2:
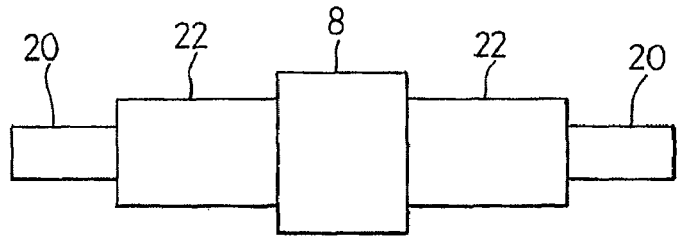
FIG. 2 is a plan view of the system of FIG. 1.
Figure 3:
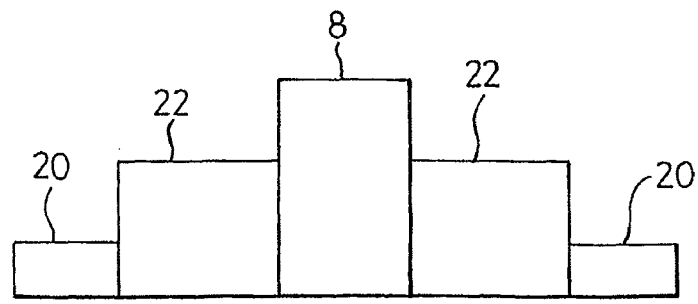
FIG. 3 is a schematic side view of the system of FIG. 1.

Referring to FIGS. 1 to 3, a concourse baggage scanning system 6 comprises a scanning unit 8 comprising a multi-focus X-ray source 10 and X-ray detector array 12. The source 10 comprises a large number of source points 14 in respective spaced locations on the source, and arranged in a full 360° circular array around the axis X-X of the system. It will be appreciated that arrays covering less than the full 360° angle can also be used.

Figure 1A:
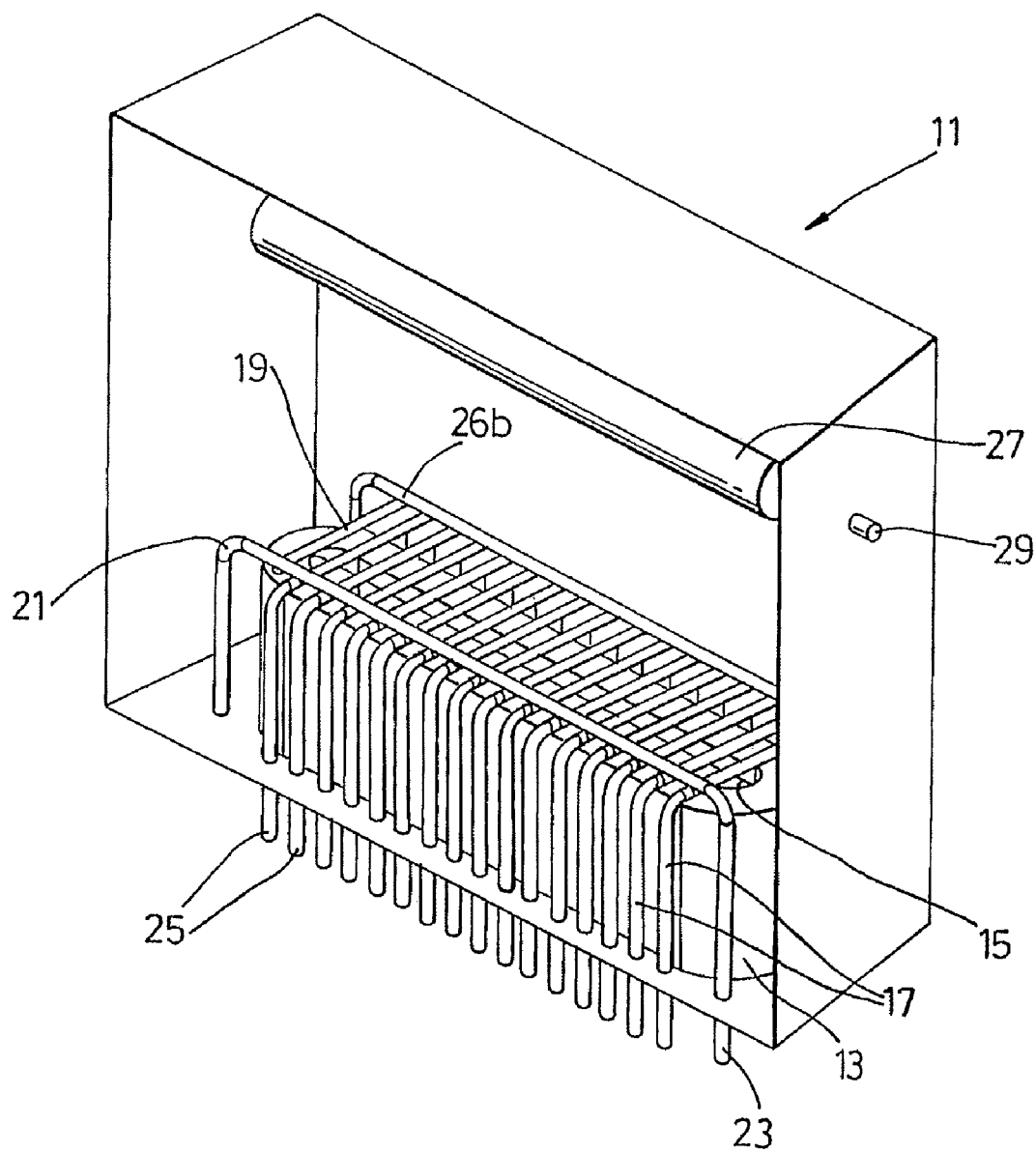
FIG. 1a is a perspective view of an X-ray source of the system of FIG. 1.

Referring to FIG. 1a, the X-ray source 10 is made up of a number of source units 11 which are spaced around the scanning region 16 in a substantially circular arrangement, in a plane perpendicular to the direction of movement of the conveyor. Each source unit 11 comprises a conductive metal suppressor 13 having two sides and an emitter element 15 extending along between the suppressor sides. A number of grid elements in the form of grid wires 17 are supported above the suppressor 13 perpendicular to the emitter element 15. A number of focusing elements in the form of focusing wires 19 are supported in another plane on the opposite side of the grid wires to the emitter element. The focusing wires 19 are parallel to the grid wires 17 and spaced apart from each other with the same spacing as the grid wires, each focusing wire 19 being aligned with a respective one of the grid wires 17.

The focusing wires 19 are supported on two support rails 21 which extend parallel to the emitter element 15, and are spaced from the suppressor 13. The support rails 21 are electrically conducting so that all of the focusing wires 19 are electrically connected together. One of the support rails 21 is connected to a connector 23 to provide an electrical connection for the focusing wires 19. Each of the grid wires 17 extends down one side of the suppressor 12 and is connected to a respective electrical connector 25 which provide separate electrical connections for each of the grid wires 17.

An anode 27 is supported above the grid wires 17 and focusing wires 19. The anode 27 is formed as a rod, typically of copper with tungsten or silver plating, and extends parallel to the emitter element 15. The grid and focusing wires 17, 19 therefore extend between the emitter element 15 and the anode 27. An electrical connector 29 provides an electrical connection to the anode 27.

The grid wires 17 are all connected to a negative potential, apart from two which are connected to a positive potential. These positive grid wires extract a beam of electrons from an area of the emitter element 15 and, with focusing by the focusing wires 19, direct the electron beam at a point on the anode 27, which forms the X-ray source point for that pair of grid wires. The potential of the grid wires can therefore be switched to select which pair of grid wires is active at any one time, and therefore to select which point on the anode 27 is the active X-ray source point at any time.

The source 10 can therefore be controlled to produce X-rays from each of the source points 14 in each of the source units 11 individually and, referring back to FIG. 1, X-rays from each source point 14 are directed inwards through the scanning region 16 within the circular source 10. The source 10 is controlled by a control unit 18 which controls the electrical potentials applied to the grid wires 17 and hence controls the emission of X-rays from each of the source points 14.

Other suitable X-ray source designs are described in WO 2004/097889.

The multi-focus X-ray source 10 allows the electronic control circuit 18 to be used to select which of the many individual X-ray source points 14 within the multi-focus X-ray source is active at any moment in time. Hence, by electronically scanning the multi-focus X-ray tube, the illusion of X-ray source motion is created with no mechanical parts physically moving. In this case, the angular velocity of source rotation can be increased to levels that simply cannot be achieved when using conventional rotating X-ray tube assemblies. This rapid rotational scanning translates into an equivalently speeded up data acquisition process and subsequently fast image reconstruction.

The detector array 12 is also circular and arranged around the axis X-X in a position that is slightly offset in the axial direction from the source 10. The source 10 is arranged to direct the X-rays it produces through the scanning region 16 towards the detector array 12 on the opposite side of the scanning region. The paths 18 of the X-ray beams therefore pass through the scanning region 16 in a direction that is substantially, or almost, perpendicular to the scanner axis X-X, crossing each other near to the axis. The volume of the scanning region that is scanned and imaged is therefore in the form of a thin slice perpendicular to the scanner axis. The source is scanned so that each source point emits X-rays for a respective period, the emitting periods being arranged in a predetermined order. As each source point 14 emits X-rays, the signals from the detectors 12, which are dependent on the intensity of the X-rays incident on the detector, are produced, and the intensity data that the signals provide are recorded in memory. When the source has completed its scan the detector signals can be processed to form an image of the scanned volume.

A conveyor belt 20 moves through the imaging volume, from left to right, as seen in FIG. 1, parallel to the axis X-X of the scanner. X-ray scatter shields 22 are located around the conveyor belt 20 upstream and downstream of the main X-ray system to prevent operator dose due to scattered X-rays. The X-ray scatter shields 22 include lead rubber strip curtains 24 at their open ends such that the item 26 under inspection is dragged through one curtain on entering, and one on leaving, the inspection region. In the integrated system shown, the main electronic control system 18, a processing system 30, a power supply 32 and cooling racks 34 are shown mounted underneath the conveyor 20. The conveyor 20 is arranged to be operated normally with a continuous scanning movement at constant conveyor speed, and typically has a carbon-fibre frame assembly within the imaging volume.

Figure 4:
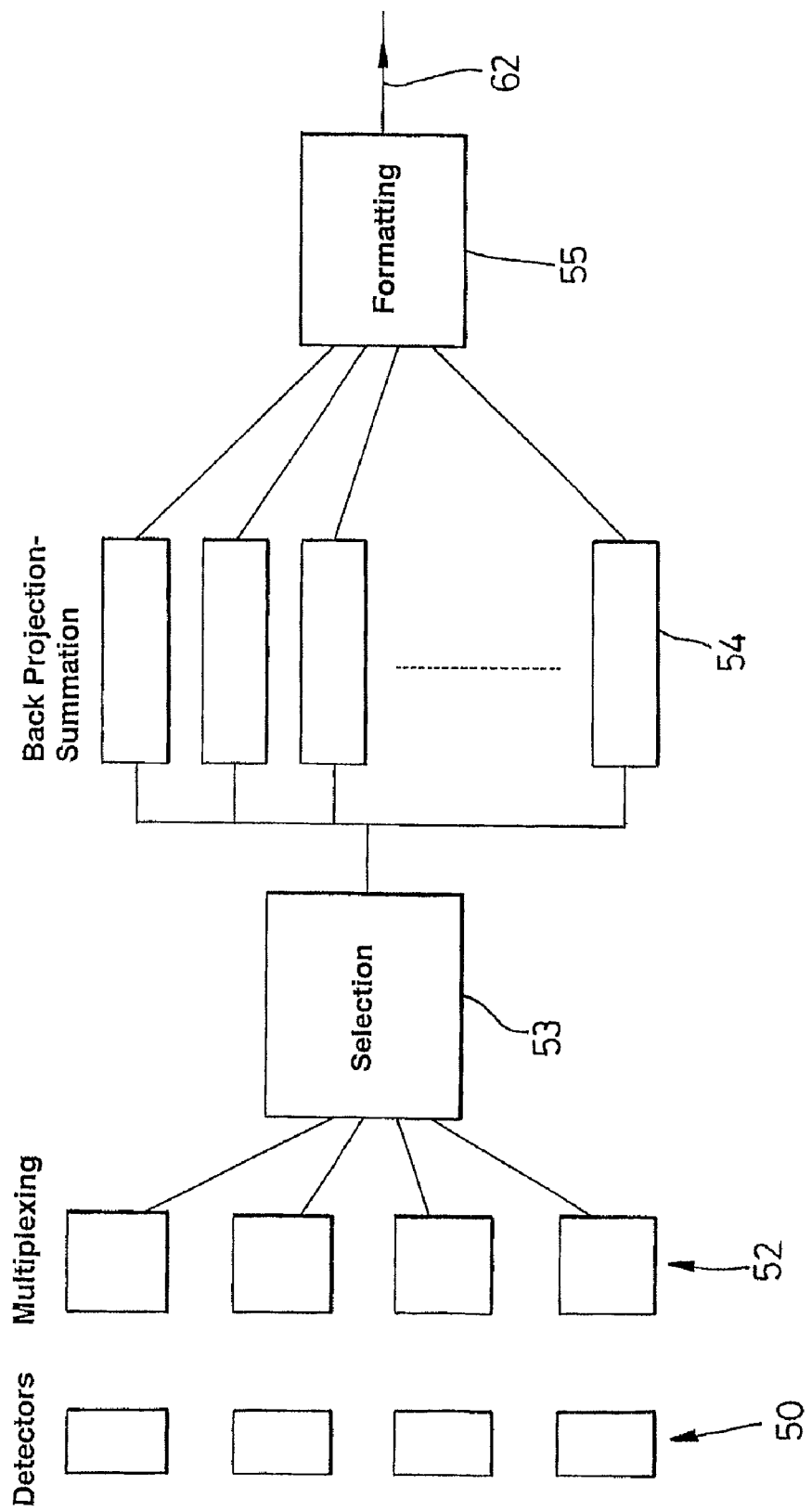
FIG. 4 is a schematic diagram of a data acquisition system forming part of the system of FIG. 1.

Referring to FIG. 4 the processing system 30 includes an electronic data acquisition system and real-time image reconstruction system. The X-ray detector array 12 comprises banks of individual X-ray detectors 50 configured in a simple linear pattern (e.g. 1×16). Multiple ring patterns (e.g. 8×16) are also possible. Each detector 50 outputs a signal dependent on the intensity of the X-rays it detects. A multiplexing block 52 multiplexes the output data signals from each of the input X-ray detectors 50, performs data filtering, gain and offset corrections and formats the data into a high-speed serial stream. A selection block 53 takes input from all of the multiplexing blocks 52 and selects just the part of the entire X-ray data that is required for the image reconstruction. The selection block 53 also determines the un-attenuated X-ray beam intensity, Io, for the appropriate X-ray source point (which will vary for every X-ray source point within the multi-focus X-ray tube), processes the X-ray intensity data, Ix, from the multiplexing block 52 by forming the result $\log_e(Ix/Io)$ and then convolves this with a suitable 1-D filter. The resulting projection data is recorded as a sinogram, in which the data is arranged in an array with pixel number along one axis, in this case horizontally, and source angle along another axis, in this case vertically. Data is then passed from the selection block 53 in parallel to a set of backprojection-summation processor elements 54. The processor elements 54 are mapped into hardware, using look-up tables with pre-calculated coefficients to select the necessary convolved X-ray data and weighting factors for fast backprojection and summation. A formatting block 55 takes the data representing individual reconstructed image tiles from the multiple processor elements 54 and formats the final output image data to a form suitable for generating a suitably formatted three dimensional image on a display screen. This output can be generated fast enough for the images to be generated in real time, for viewing in real time or off-line, hence the system is termed a real time tomography (RTT) system.

In this embodiment the multiplexing block 52 is coded in software, the selection block 53 and formatting block 55 are both coded in firmware, and the processor elements mapped in hardware. However, each of these components could be either hardware or software depending on the requirements of the particular system.

Figure 5:
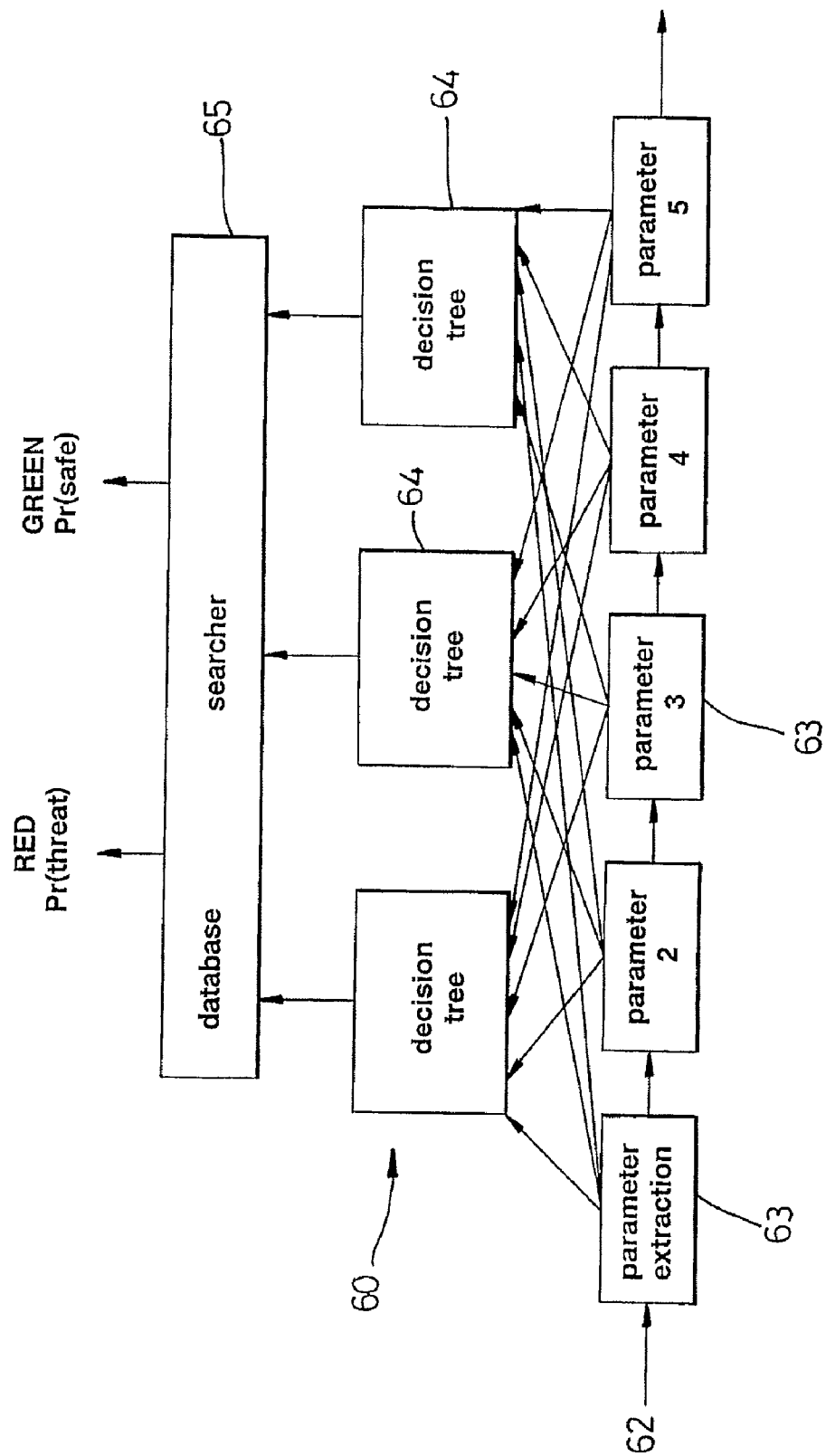
FIG. 5 is a schematic diagram of a threat detection system forming part of the system of FIG. 1.

Referring to FIG. 5 each of the final output image for each baggage item is then processed by a threat detection processor 60 within the processing system 30 which is arranged to determine whether the imaged baggage item represents a threat. In the threat detection processor 60, input X-ray tomographic image data 62 is passed in to a set of low-level parameter extractors 63 (level 1). The parameter extractors 63 identify features in the image such as areas of constant grey level, texture and statistics. Some of the extractors work on the data for individual 2 dimensional images or slices, some work on the 3 dimensional images, and some work on the sonogram data. Where possible, each extractor works in parallel on the same set of input data, and each extractor is arranged to perform a different processing operation and to determine a different parameter. At the end of the processing, the parameters determined by the parameter extractors 63 are passed up to a set of decision trees 64 (level 2). Details of the parameters extracted are given below. The decision trees 64 each take a number (typically all) of the low level parameters and construct respective higher level information, such as information regarding contiguous volumes, with associated statistics. At the top level (level 3), a database searcher 65 maps the higher level parameters produced at level 2 into a 'red' probability Pr(threat) of there being a threat present and a 'green' probability Pr(safe) of the item under inspection being safe. These probabilities are used by the processing system 30 to allocate the scanned item to an appropriate safety category, and to produce an automatic sorting control output. This automatic sorting control output can be either a first 'green' output indicating that the item is allocated to a clear category, a second 'red' output indicating that the item is allocated to a 'not clear' category, or a third 'amber' output indicating that the automatic sorting cannot be carried out with sufficient reliability to allocated the item to the 'clear' or the 'not clear' category. Specifically if Pr(safe) is above a predetermined value, (or Pr(threat) is below a predetermined value) then the automatic sorting output will be produced having a first signal form, indicating that the item should be allocated to the green channel. If Pr(threat) is above a predetermined value, (or Pr(safe) is below a predetermined value) then the automatic sorting output will be produced having a second signal form, indicating that the item should be allocated to the red channel. If Pr(threat) (or Pr (safe)) is between the two predetermined values, then the automatic sorting output is produced having a third signal form, indicating that the item cannot be allocated to either the red or green channel. The probabilities can also be output as further output signals.

The parameters that will be determined by the parameter extractors 63 generally relate to statistical analysis of pixels within separate regions of the 2-dimensional or 3-dimensional image. In order to identify separate regions in the image a statistical edge detection method is used. This starts at a pixel and then checks whether adjacent pixels are part of the same region, moving outwards as the region grows. At each step an average intensity of the region is determined, by calculating the mean intensity of the pixels within the region, and the intensity of the next pixel adjacent to the region is compared to that mean value, to determine whether it is close enough to it for the pixel to be added to the region. In this case the standard deviation of the pixel intensity within the region is determined, and if the intensity of the new pixel is within the standard deviation, then it is added to the region. If it is not, then it is not added to the region, and this defines the edge of the region as being the boundary between pixels in the region and pixels that have been checked and not added to the region.

Once the image has been divided into regions, then parameters of the region can be measured. One such parameter is a measure of the variance of the pixel intensity within the region. If this is high this might be indicative of a lumpy material, which might for example be found in a home-made bomb, while if the variance is low this would be indicative of a uniform material such as a liquid.

Another parameter that is measured is the skewedness of the distribution of pixel value within the region, which is determined by measuring the skewedness of a histogram of pixel values. A Gaussian, i.e. non-skewed, distribution indicates that the material within the region is uniform, whereas a more highly skewed distribution indicates non-uniformities in the region.

As described above, these low-level parameters are passed up to the decision trees 64, where higher level information is constructed an higher level parameters determined. One such higher level parameter is the ratio of the surface area to the volume of the identified region. Another is a measure of similarity, in this case cross-correlation, between the shape of the region and template shapes stored in the system. The template shapes are arranged to correspond to the shape of items that pose a security threat, such as guns or detonators. These high level parameters are used as described above to determine a level If threat posed by the imaged object.

Figure 6:
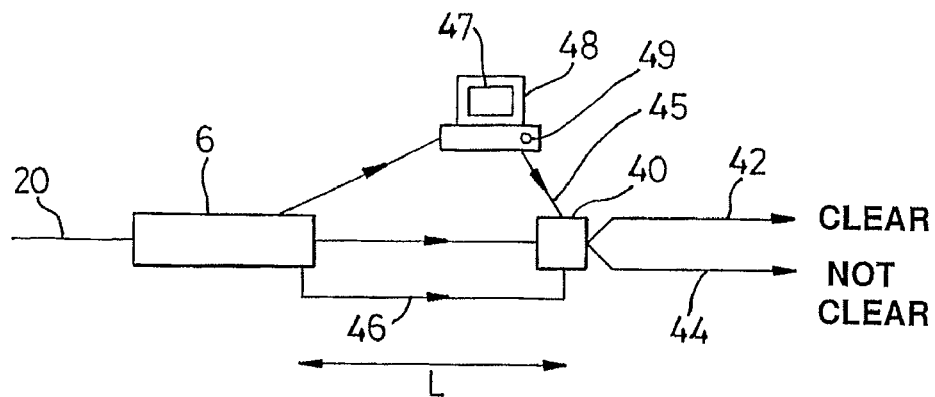
FIG. 6 is a schematic diagram of a baggage sorting system according to an embodiment of the invention including the scanning system of FIG. 1.

Referring to FIG. 6 an in-line real time tomography baggage sorting system comprises the scanning system 6 of FIG. 1 with the conveyor 20 passing through it. Downstream of the scanning system 6 a sorting device 40 is arranged to receive articles of baggage from the conveyor 20 and move them onto either a clear or 'green' channel conveyor 42 or a not clear or 'red' channel conveyor 44. The sorting device 40 is controlled by the automatic sorting output signals via a control line 46 from the processing system 30, which are indicative of the decision of the processing system 30 as to whether the item is clear or not, and also by signals from a workstation 48 to which it is connected via line 45. The images from the scanning system 6 and signals from the processing system 30, indicative of the red and green probabilities and the nominal decision of the processing system 30, are also fed to the workstation 48. The workstation is arranged to display the images on a screen 47 so that they can be viewed by a human operator, and also to provide a display indicative of the green and red probabilities and the nominal automatic sorting decision. The user at the workstation can review the images and the probabilities, and the automatic sorting output, and decide whether to accept or override the decision of the scanning system, if that was to allocate the item to the red or green category, or to input a decision if the scanning system decision was to allocate the item to the 'amber' category. The workstation 48 has a user input 49 that enables the user to send a signal to the sorting device 40 which can be identified by the sorting device as over-riding the decision of the scanning system. If the over-riding signal is received by the sorting device, then the sorting device does over-ride the decision of the scanning system. If no over-ride signal is received, or indeed if a confirming signal is received from the workstation confirming the decision of the scanning system, then the sorting device sorts the item on the basis of the decision of the scanning system. If the sorting system receives an 'amber' signal from the scanning system relating to an item, then it initially allocates that item to the 'red' category to be put into the red channel. However, if it receives an input signal from the workstation before it sorts the item indicating that it should be in the 'green' category, then it sorts the item to the green channel.

In a modification to the system of FIG. 6, the sorting can be fully automatic, with the processing system giving one of just two sorting outputs, 'clear' and 'not clear', allocating the item to either the green or the red channel. It would also be possible for the processing system to determine just one probability Pr(threat) with one threshold value and allocate the item to one of the two categories depending on whether the probability is above or below the threshold. In this case the allocation would still be provisional and the operator would still have the option of overriding the automatic sorting. In a further modification the automatic category allocation of the scanning system is used as the final allocation, with no user input at all. This provides a fully automated sorting system.

In the system of FIG. 6, the scan speed is matched to the conveyor velocity, so that the baggage can be moved at a constant velocity from a loading area where it is loaded onto the conveyor 20, through the scanning system 6, and on to the sorting device 40. The conveyor 20 extends for a distance L, between the exit of the scanning system 6 and the sorting device 40. During the time that a baggage item takes to travel the distance L on the conveyor 20, an operator can view the image data of the item under inspection, and the initial category allocation determined by the scanning system, and confirm or reject the automated decision of the RTT system. Typically the baggage would then be either accepted into the Clear channel and passed forward ready for transportation or rejected into the Not Cleared channel for further investigation.

In this RTT multi-focus system, the RTT scanning unit 8 is able to operate at full baggage belt speed, and hence no baggage queuing or other divert mechanism is required for optimal system operation. In integrated systems such as this, the limited throughput capability of conventional rotating source systems is a significant constraint. Often this means placing multiple conventional CT machines in parallel, and using sophisticated baggage handling systems to switch the item for inspection to the next available machine. This complexity can be avoided with the arrangement of FIG. 6.

Figure 7:
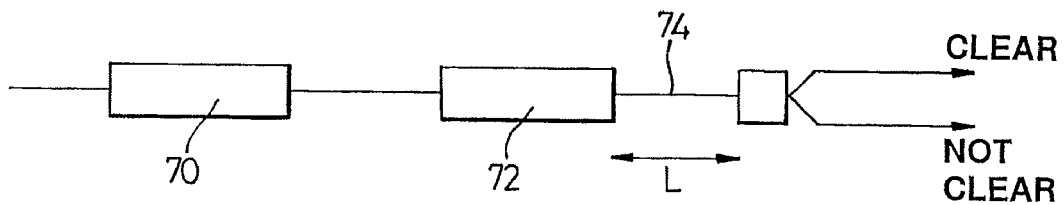
FIG. 7 is a schematic diagram of a baggage sorting system according to a further embodiment of the invention.

Referring to FIG. 7 a second embodiment of the invention comprises a redundant system in which two RTT scanning systems 70, 72 are located in series on the same conveyor 74 such that if one system were to be taken out of service, then the other could continue to scan baggage. In either case, the conveyor belt 74 would continue to run through both scanning systems 70, 72 at standard operating belt speed.

Figure 8A:
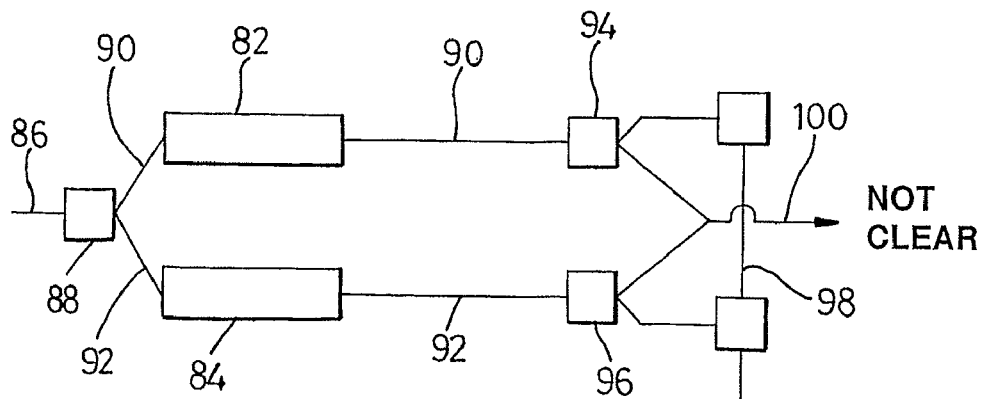
Figure 8B:
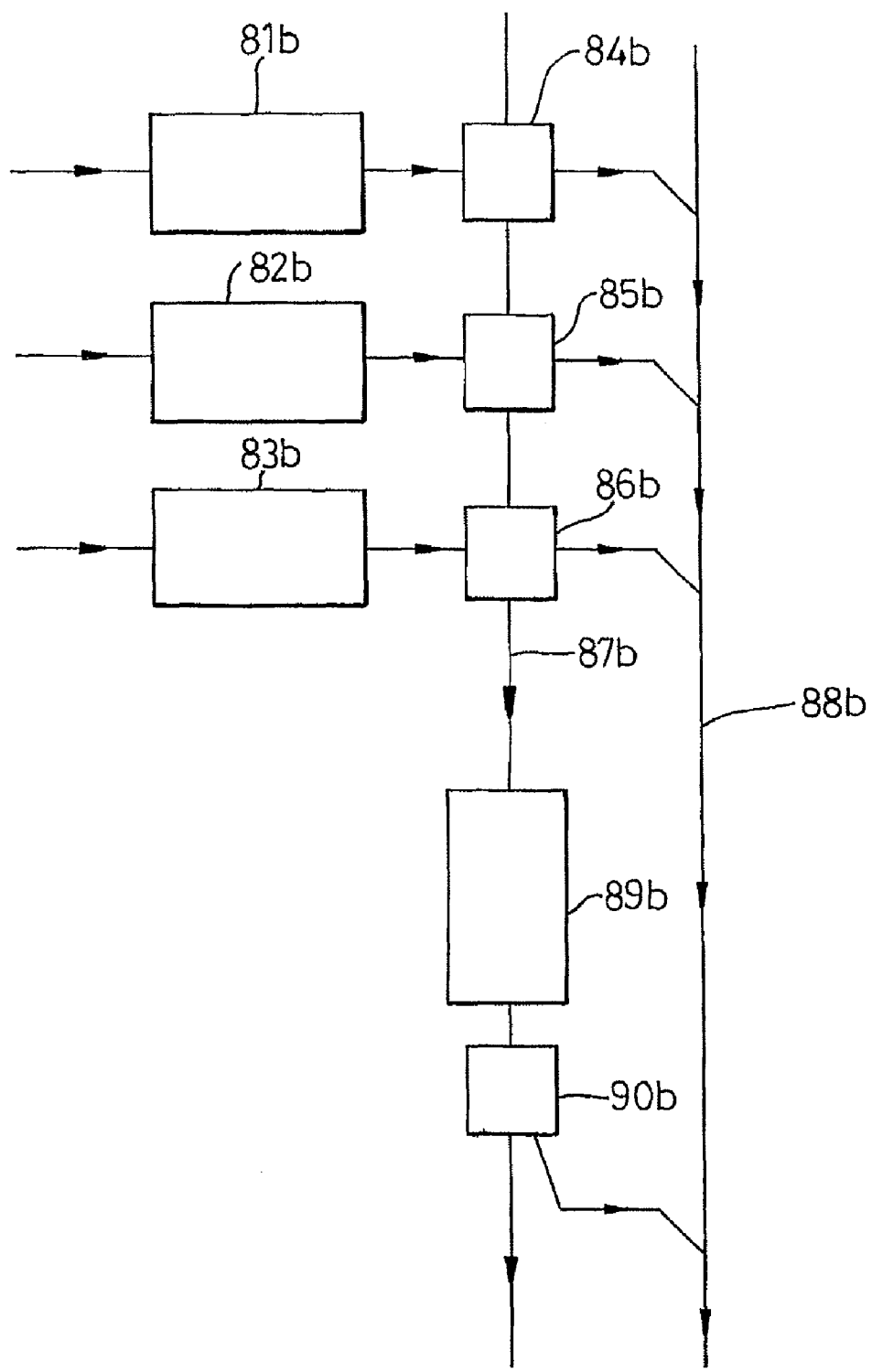

Referring to FIG. 8a in a third embodiment there is provided a more complex redundant system in which two RTT systems 82, 84 are operated in parallel. A first main incoming conveyor 86 brings all items to be sorted to a first sorting device 88 which can transfer items onto either one of two further conveyors 90, 92. Each of these two conveyors 90, 92 passes through a respective one of the scanning systems 82, 84, which will scan the items and enable a decision to be made as to whether to clear the item or not. A further sorting device 94, 96 is provided on each of the two conveyors 90, 92 which is arranged to sort the baggage onto a common 'green channel' conveyor 98 for onward transportation, or a 'red channel' conveyor 100 if it is not cleared, where it can undergo further investigation. In this configuration, it is possible to run the input conveyor 86, and the 'green channel' conveyor at a higher speed than the RTT conveyor speed, typically up to twice the speed. For example in this case the main incoming conveyor 86 and the common 'green channel' conveyor move at a speed of 1 m/s whereas the scanning conveyors 82, 84 travel at half that speed, i.e. 0.5 m/s. Of course the system can be expanded with more parallel RTT systems, with the ratio of the speed of the main incoming conveyor to that of the scanner conveyors being equal to, or substantially equal to, the number of parallel scanners, although the sorting devices may become unreliable at more than about 1 m/s main conveyor speed.

Referring to FIG. 5b, in a further embodiment a baggage sorting system comprises a number of RTT scanners 81b, 82b, 83b, typically up to about 60 in one system, each associated with a respective check-in desk. A sorting device 84b, 85b, 86b is associated with each RTT scanner, and baggage is conveyed on a conveyor from each RTT scanner to its associated sorting device. Each sorting device 84b, 85b, 86b sorts the baggage, in response to signals from its scanner, onto either a common clear channel conveyor 88b, or a common reject channel conveyor 87b. A further backup RTT scanner 89b is provided on the reject channel conveyor 87b, with an associated sorting device 90b, that can leave baggage on the reject channel conveyor 87b, or transfer it to the clear channel conveyor 88b.

Under normal operation, each of the primary scanners 81b, 82b, 83b sorts the baggage, and the backup or redundant scanner 89b simply provides a further check on items sorted into the reject channel. If that scanner determines that an item of baggage represents no, or a sufficiently low threat, then it transfers it to the clear channel. If one of the primary scanners is not functioning or has a fault, then its associated sorting device is arranged to sort all baggage from that scanner to the reject channel. Then, the back-up scanner 89b scans all of that baggage and controls sorting of it between the clear and reject channels. This enables all the check-in desks to continue to function while the faulty scanner is repaired or replaced.

Referring to FIG. 8c, in a further embodiment, baggage from each of the check-in desks is transferred via a plurality of separate conveyors onto a central loop or carousel 81c, on which it circulates continuously. A number of sorting devices 82c, 83c, 84c are each arranged to transfer items of baggage from the loop 81c to a respective conveyor leading to a respective RTT scanner 85c, 86c, 87c. The sorting devices 82c, 83c, 84c are controlled by the scanners to control the rate at which baggage items are fed to each of the scanners. From the scanners, conveyors transfer all of the baggage items to a common exit conveyor 88c leading to a further sorting device 89c. This is controlled by all of the scanners to sort each of the baggage items between a clear channel 90c and a reject channel 91c.

In order to track the movement of each item of baggage, each item is given a 6-digit ID, and its position on the conveyor recorded when it first enters the system. The scanners can therefore identify which item of baggage is being scanned at any one time, and associate the scanning results with the appropriate item. The sorting devices can therefore also identify the individual baggage items and sort them based on their scanning results.

The number of scanners and the speeds of the conveyors in this system are arranged such that, if one of the scanners is not functioning, the remaining scanners can process all of the baggage that is being fed onto the loop 81c from the check-in desks.

In a modification to this embodiment, the sorting devices 82c, 83c, 84c that select which items are transferred to each scanner are not controlled by the scanners, but are each arranged to select items from the loop 81c so as to feed them to the respective scanner at a predetermined rate.

Figure 9:
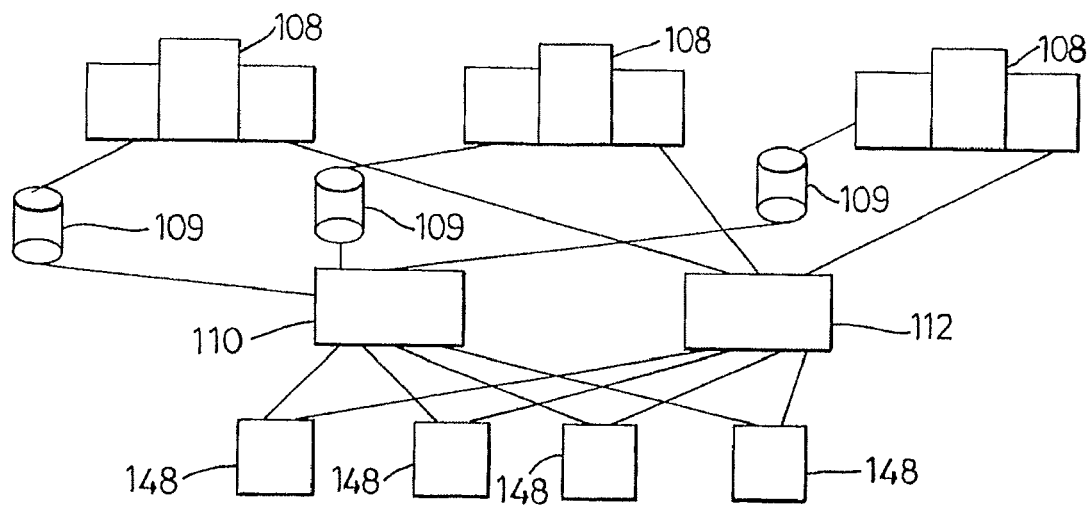
FIG. 9 is a schematic diagram of a networked baggage sorting system according to a further embodiment of the invention.

Referring to FIG. 9 a networked system according to a further embodiment comprises three scanning systems 108 similar to that of FIG. 6, and four operator workstations 148. The video image outputs from the three RTT scanning systems 108 are connected via respective high bandwidth point-to-point video links to real time disk arrays 109 which providing transient storage for the raw image data, to a redundant video switch 110. The disk arrays 109 are in turn connected to each of the workstations 148. The video switch 110 is therefore able to transmit the raw video image output from each of the scanning systems 108 from its temporary storage, to any one of the workstations 148, where it can be used to create 3-dimensional video images which can be viewed off-line. The outputs from the scanning system for the red/green probability signals and the automatic sorting allocation signals are connected to a redundant conventional Ethernet switch 112, which is also connected to each of the workstations. The Ethernet switch is arranged to switch each of the probability signals and the sorting allocation signals to the same workstation 148 as the associated video signal. This allows image data from the multiple machines together with the automatic allocation and probabilities assigned to the allocation, to be switched through to the bank of operator workstations 148 where an operator can both monitor the performance of the baggage inspection system and determine the destination of baggage assigned an amber threat level.

Alternatively, a networked system comprises a single scanning system 108 connected to, a server and a workstation 148. The video image output, from the scanning system 108 is connected to a real time disk array 109, which provides transient storage for the raw image data. The disk array 109 is in turn connected to the workstation 148. The probability signal and allocation signal outputs are sent to the workstation 148 together with the associated video image output to be monitored by an operator. The networked single scanning system may be part of a networked system with multiple scanning systems.

Figure 10:
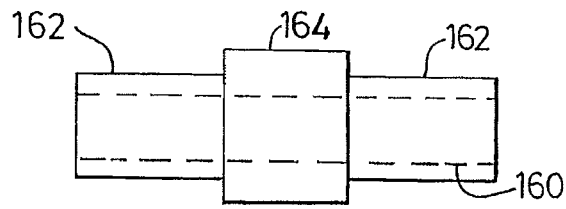
FIG. 10 is a schematic plan view of a stand-alone scanning system according to a further embodiment of the invention.
Figure 11:
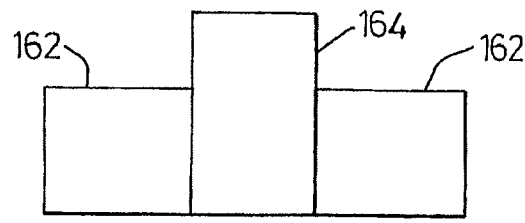
FIG. 11 is a schematic side view of the system of FIG. 10.

Referring to FIGS. 10 and 11, in a further embodiment an in-line scanner has a conveyor belt 160 just as long as the main scatter shields 162. In such standalone system configurations, the item for inspection is placed onto the conveyor belt 160 and the item loaded into the system. The item is then scanned through the scanner machine 164 and images are generated. Often, in conventional systems, the item is pre-screened with a simple transmission X-ray system to identify likely threat areas prior to computed tomography screening of selected planes in the object. Such applications are simple for a real-time multi-focus system to cope with. Here, no pre-screening would be used and a true three-dimensional image of the complete item would be obtained.

In some embodiments the locus of source points in the multi-focus X-ray source will extend in an arc over an angular range of only 180 degrees plus the fan beam angle (typically in the range 40 to 90 degrees). The number of discrete source points is advantageously selected to satisfy the Nyquist sampling theorem. In some embodiments, as in that of FIG. 1, a complete 360 degree ring of source points is used. In this case, the dwell-time per source point is increased over a 180+fan beam configuration for a given scan rate and this is advantageous in improving reconstructed image signal-to-noise ratio.

Figure 12:
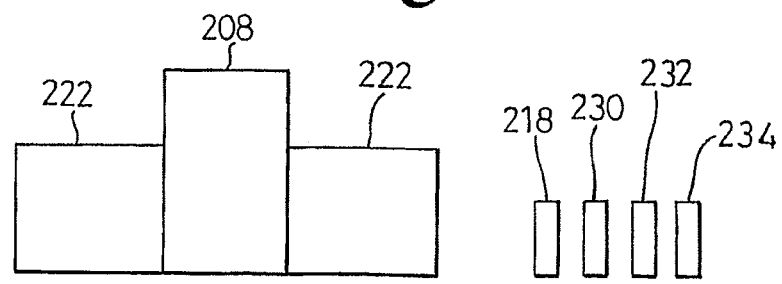
FIG. 12 is a schematic side view of a modular scanning system according to a further embodiment of the invention.

The scanner system of FIG. 1 is an integrated scanner system, in that, the control, processing, power supply, and cooling units 18, 30, 32, 34 are housed in a unit with the scanning system 8 and the screening 22. Referring to FIG. 12, in a further embodiment there is provided a modular system in which some, or all, of the control, processing, power supply, and cooling racks 218, 230, 232, 234 are located remotely from the scanning unit 208 comprising multi-focus X-ray source and sensor array. It is advantageous to use a modular design to facilitate easy installation, particularly in baggage handling hall environments, where systems may be suspended from the ceiling or in regions with restricted access. Alternatively, a complete system can be configured as an integrated unit with the sub-assembly units co-located within a single housing.

In some embodiments, including that of FIG. 1, a single X-ray detector ring is used. This is inexpensive to construct and provides adequate signal-to-noise performance even at high image scanning rates with a simple fan-beam image reconstruction algorithm. In other embodiments (particularly for large image reconstruction circle diameter) it is preferable to use a multi-ring sensor array with a plurality of circular or part-circular groups of sensors arranged adjacent to each other, spaced along the axis of the system offset from the source. This enables a more complex cone-beam image reconstruction algorithm to be used in the processing system. The use of a multi-ring sensor increases dwell-time per source point resulting in larger integrated signal size and consequent improvement in signal-to-noise ratio in the reconstructed image.

Central to the design of the embodiments described above, which use a multi-focus X-ray source based computed tomography system, is the relationship between the angular rotational speed of the source and the velocity of the conveyor system passing through the scanner. In the limit that the conveyor is stationary, the thickness of the reconstructed image slice is determined entirely by the size of the X-ray focus and the area of the individual elements of the X-ray detector array. As conveyor speed increases from zero, the object under inspection will pass through the imaging slice during rotation of the X-ray beam and an additional blurring will be introduced into the reconstructed image in the direction of the slice thickness. Ideally, the X-ray source rotation will be fast compared to the conveyor velocity such that blurring in the slice thickness direction will be minimised.

A multi-focus X-ray source based computed tomography system for baggage inspection provides a good ratio of angular source rotational speed to linear conveyor speed for the purposes of high probability detection of threat materials and objects in the item under inspection. As an example, in the embodiment of FIG. 1, the conveyor speed is 0.5 m/s as is common in airport systems. The source can achieve 240 source rotations about the conveyor per second, so the object under inspection will move a distance of 2.08 mm through the imaging slice during the scan. In a conventional system with source rotation of 4 revolutions per second, the object under inspection will move a distance of 62.5 mm through the imaging slice during the scan at the same belt speed.

The primary goal of an inspection system for detection of threat materials is to detect accurately the presence of threat materials and to pass as not suspect all other materials. The larger the blurring in the slice direction that is caused by conveyor motion during a scan, the greater the partial volume artefact in the reconstructed image pixel and the less accurate the reconstructed image density. The poorer the accuracy in the reconstructed image density, the more susceptible the system is to provide an alarm on non-threat materials and to not raise an alarm on true threat materials. Therefore, a real-time tomography (RTT) system based on multi-focus X-ray source technology can provide considerably enhanced threat detection capability at fast conveyor speeds than conventional mechanically rotated X-ray systems.

Due to the use of an extended arcuate anode in a multi-focus X-ray source, it is possible to switch the electron source such that it jumps about the full length of the anode rather than scanning sequentially to emulate the mechanical rotation observed in conventional computed tomography systems. Advantageously, the X-ray focus will be switched to maximise the distance of the current anode irradiation position from all previous irradiation positions in order to minimise the instantaneous thermal load on the anode. Such instantaneous spreading of the X-ray emission point is advantageous in minimising partial volume effect due to conveyor movement so further improving reconstructed pixel accuracy.

The high temporal resolution of RTT systems allows a high level of accuracy to be achieved in automated threat detection. With this high level of accuracy, RTT systems can be operated in unattended mode, producing a simple two-state output indication, with one state corresponding to a green or clear allocation and the other to a red or not clear allocation. Green bags are cleared for onward transport. Red bags represent a high level of threat and should be reconciled with the passenger and the passenger barred from travelling.

Further embodiments of the invention will now be described in which data relating to the scattering of X-rays as well as that relating to transmitted X-rays is recorded and used to analyse the scanned baggage items.

Figure 13:
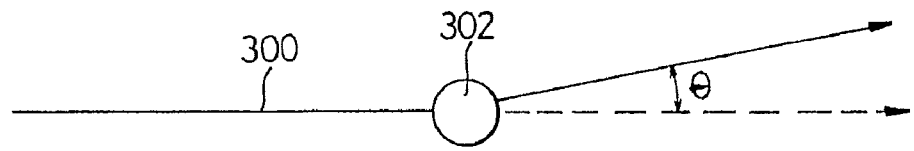
FIG. 13 is a diagram of an X-ray scattering event.

Referring to FIG. 13 when a beam 300 of X-rays passes through an object 302, some of the X-rays are transmitted straight through it, and exit the object travelling in the same direction as they entered it. Some of the X-rays are scattered through a scattering angle $\theta$, which is the difference between the direction in which they enter the object and the direction in which they leave it. As is well known there are two types of scattering that occur: coherent or Bragg scattering, which is concentrated around scattering angles of 5°, typically in the range 4° to 6°, and incoherent or Compton scattering in which the X-ray is scattered through larger angles. Bragg scattering increases linearly with the atomic number of the object and obeys the formula:

$$n\lambda = 2d \sin \theta$$

where
n is an integer
$\lambda$ is the wavelength of the X-ray
d is the inter-atomic distance in the object.

Therefore the amount of Bragg scattering gives information about the atomic structure of the object. However, it does not vary smoothly with atomic number.

The amount of Compton scattering is dependent on, and varies smoothly with, the electron density of the object, and therefore the amount of scattering at higher scatter angles gives information about the electron density of the object, and hence about its atomic number.

Figure 14:
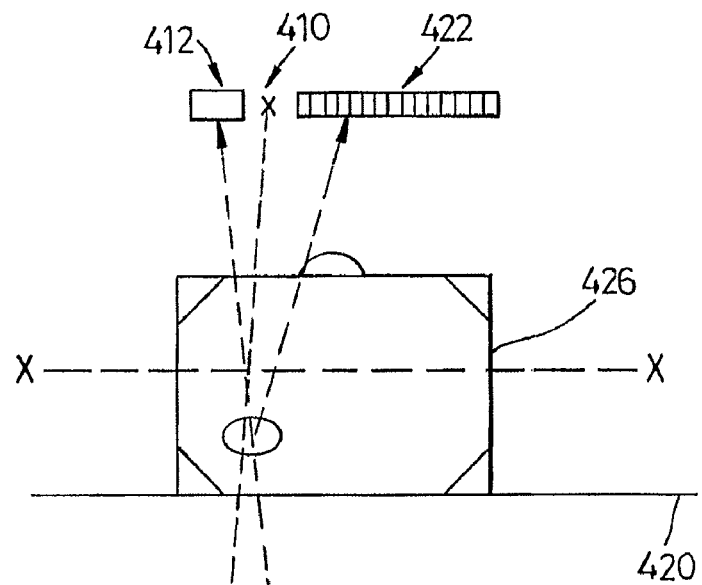
FIG. 14 is a longitudinal section through a security scanning system according to a further embodiment of the invention.

Referring to FIG. 14 a security scanning system according to a further embodiment of the invention comprises a multi-focus X-ray source 410 which is the same as that of FIG. 1, and a circular detector array 412 and conveyor 420 that are also the same as those of FIG. 1. However, in this embodiment, the system comprises a further cylindrical array of detectors 422 which also extends around the conveyor at the same radius as the circular detector array 412 but on the other side axially of the source 410. Whereas the circular detector array is arranged to detect X-rays transmitted through the object 426, the cylindrical detector array 422 is arranged to detect X-rays scattered in the object. The scatter detector array 422 is made up of a number of circular arrays or rings 422a, 422b of detectors, and the detectors in each ring are equally spaced around the conveyor so that they are arranged in a number of straight rows extending in the axial direction of the scanner.

The detectors in the scatter detector array 422 are energy resolving detectors such that individual X-ray interactions with each detector produce a detector output that is indicative of the energy of the X-ray. Such detectors can be fabricated from wide bandgap III-V or II-IV semiconductor materials such as GaAs, HgI, CdZnTe or CdTe, a narrow gap semiconductor such as Ge, or a composite scintillation detector such as NaI(Ti) with photomultiplier tube readout.

Figure 15:
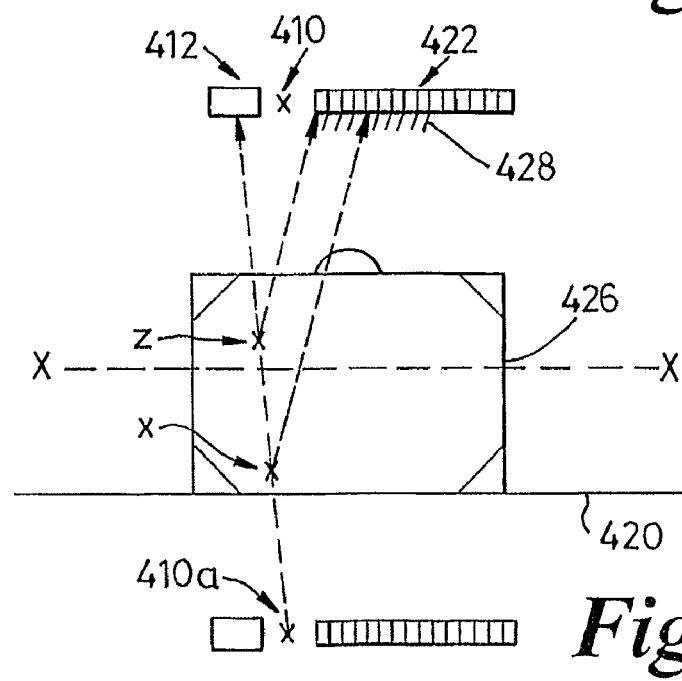
FIG. 15 is a further longitudinal section through the system of FIG. 14 showing how different scatter events are detected.
Figure 16:
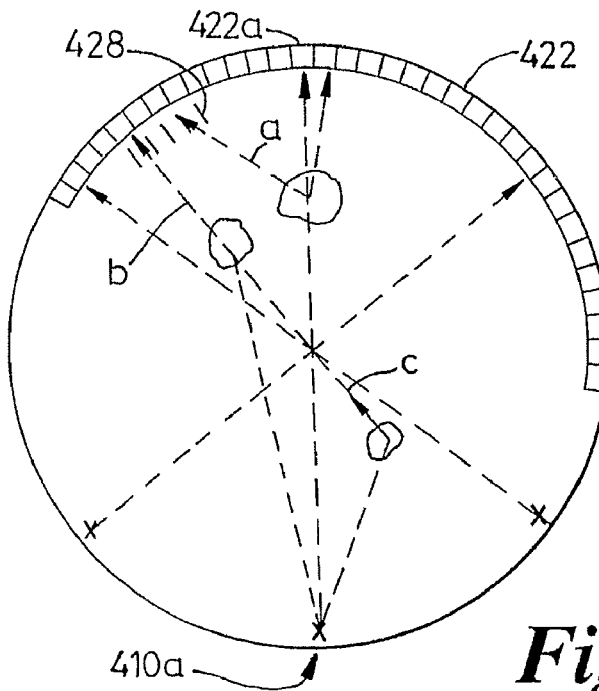
FIG. 16 is a transverse section through the system of FIG. 14.

Referring to FIG. 15, a collimator 428 is provided in front of the scattering detectors 422. The collimator 428 provides a barrier that prevents X-rays from reaching each detector unless it comes from a particular receiving direction. For each detector in the array 422, the receiving direction passes through the central longitudinal axis X-X of the scanner, as can be seen in FIG. 16. However, the receiving direction is not perpendicular to the axis X-X, but is inclined at about 5° to the plane of the detector rings 422a, 422b in the direction towards the source 410, as can be seen in FIG. 15.

Referring to FIG. 15 it will be appreciated that X-rays incident on any one of the detectors of the array 422 must have been scattered from a respective small sub-volume within the thin imaged volume that lies both in the path of the X-ray beam and in the line of the receiving direction from the detector 422. For any coherently scattered X-rays, the axial position of the detector that detects it will be determined by the distance from the active X-ray source point at which the scattering occurred. Detectors nearest the source 410 in the axial direction will detect X-rays scattered furthest from the active X-ray source point. For example X-rays scattered from the point x, which is nearest the active X-ray source point 410a, will be detected by a detector further from the source 410 than X-rays scattered from the point z which is further from the active X-ray source point. Therefore, at any one time, when the active X-ray source point can be identified, the axial position of the detector which detects the scattered X-ray can be used to determine the position of the scattering along the X-ray beam direction.

It will also be appreciated from FIG. 15 that, for this system to work, it is important that the X-ray beam should be narrowly focused in the axial direction of the scanner. Spreading of the beam in the transverse direction, e.g. use of a fan beam spread in the transverse direction will still allow this positioning of coherent scattering events.

Referring to FIG. 16, because the collimator 428 is directed towards the axis of the scanner, X-rays from an active source point 410a that undergo coherent scattering will only be detected by the row of detectors 422a that is on the opposite side of the scanner axis to the active source point, and possibly one or more of the rows close to it on either side depending on how narrowly focussed the collimator is. If X-rays are confined to a straight narrow 'pencil' beam, then any X-rays that are scattered incoherently through larger angles will not be detected at all as they will be cut off by the collimator 428. An example of such an X-ray is shown by arrow 'a' in FIG. 16. However, if a fan beam of X-rays is produced from the active source point 410a, that is spread out through the imaging volume slice in the direction perpendicular to the scanner axis, then X-rays directed further away from the scanner axis can undergo incoherent scattering and reach detectors to either side of the row 422a opposite the active source point.

Examples of such X-rays are shown by the arrows b and c. It will be noted that, to reach any detector 422b, the scattering event must take place in the plane passing through the scanner axis and that detector 422b. This means that, for a given active source point and a particular detector, the position of the scattering event of a detected X-ray can be identified as being in the plane passing through the scanner axis and that detector. If the exact position of the scattering event is to be determined then other information is needed. For example if information regarding the position of objects within the imaging volume is available, for example from tomographic imaging data, then the scattering can be associated with the most likely object as will be described in more detail below.

From the Bragg scattering data, for each detected scattering event, the combination of the X-ray energy and the scatter angle can be used to determine the inter-atomic distance d of the material in which the scattering event took place. In practice, the scatter angle can be assumed to be constant, and the energy used to distinguish between different materials. For the Compton scattering, the level of scattering from each volume of the scanning volume gives an indication of the density of the material in that volume. The ratio of Compton to coherent scatter can also be determined and used as a further parameter to characterise the material of the imaged object.

Due to the short dwell time for each X-ray source point, the number of detected scattered X-rays for each source point will always be very low, typically less than five. In order to form a reasonable coherent scatter signal it is necessary to collect scatter data for all source points within a tomographic scan and then accumulate the results for each sub-volume of the imaging volume. For a scanner with 500 source points, and an average of one coherent diffraction scatter result per sub-volume per scan, then following accumulation of the set of data, each sub-volume will have 500 results associated with it, corresponding to 500 scattering events within that sub-volume. A typical sub-volume occupies an area within the imaging plane of a few square centimeters, with a volume thickness of a few millimeters.

Figure 17:
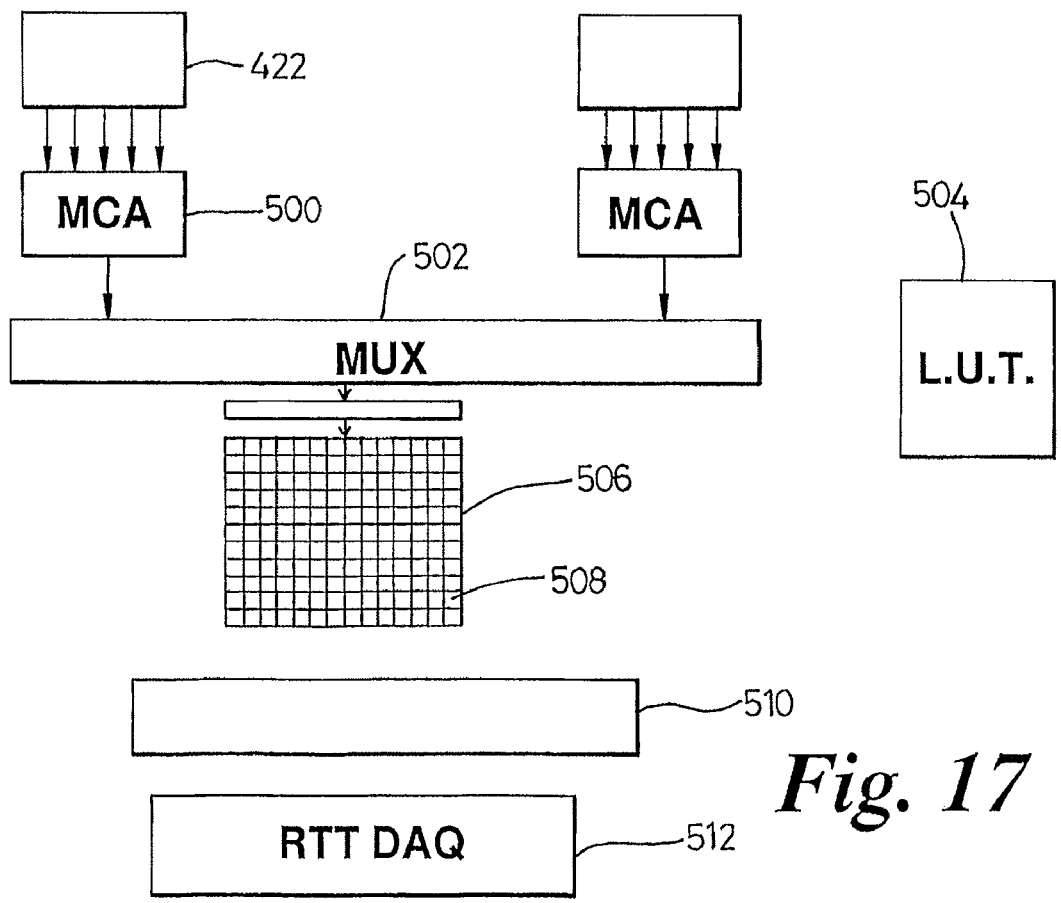
FIG. 17 is a schematic diagram of a data acquisition system of the scanning system of FIG. 14.

Referring to FIG. 17, the data acquisition system arranged to accumulate data from the scatter detector array 422 of the scanner of FIGS. 14 to 16 comprises a multi-channel analyser 500 associated with each of the detectors 422. Each MCA 500 is arranged to receive the output signals from the detector, and allocate each X-ray detected to one of a number of X-ray energy ranges or channels, and output a signal indicative of the energy range in which the detected X-ray falls. A multiplexer 502 is arranged to receive the outputs from each of the MCAs 500. A look-up table 504 is also provided which has entries in it that, for a given source point and detector, identify the sub-volume within the imaging volume in which the X-ray was scattered. The system further comprises an image memory 506 which includes a number of memory areas 508, each of which is associated with a respective sub-volume within the scanner imaging plane.

Data is loaded into each memory area 508 automatically by the multiplexer 502 under the direction of the look up table 504. The look up table is loaded with coefficients prior to scanning that map each combination of detector 422 and MCA 500 to a respective image location 508, one look up table entry per X-ray source position. Those pixels, i.e. detectors 422, that are in the forward direction, i.e. substantially in the direction that the photon is travelling from the source prior to any interaction, are assumed to record coherent scatter photons at small beam angles of about 4-6 degrees. Those pixels 422 that are not in the forward direction are assumed to record incoherent scattered photons due to the Compton scattering effect. Hence, the image memory 506 is actually "three dimensional"—two dimensions represent location in the image while the third dimension holds scattered energy spectra for both coherent (lo 8-bits) and incoherent scattering (hi 8 bits). The look up table 504 will also instruct the multiplexer 502 as to the type of data that is being collected for each MCA 500 at each projection so that the appropriate memory space is filled.

Once the scatter data has been collected for a given scan, the data is transferred to and synchronised, by a projection sequencer 510, with the main RTT data acquisition system 512, which is described above with reference to FIG. 4. Hence the reconstructed image data and scatter data are passed through simultaneously to the threat detection system, which can use it to determine suitable parameters for analysis.

For each scan, the tomographic image data from the transmission detectors 412 produces data relating to the X-ray attenuation for each pixel of the image, which in turn corresponds to a respective sub-volume of the tomographic imaging volume. This is obtained as described above with reference to FIG. 4. The data from the scatter detectors 422 provides, as described above, data relating to the amount of coherent scattering within each sub-volume, and data relating to the amount of incoherent scattering within each sub-volume. This data can therefore be analysed in a threat detection processor similar to that of FIG. 5. In this case the parameters of the data which are extracted can relate to the image data or the scatter data or combinations of two or more types of data. Examples of parameters that are extracted from the data are the ratio of coherent to incoherent scatter, material types as determined from coherent scatter data, material density as determined from incoherent scatter data, correlation of CT image pixel values with scatter data. Also parameters for the scatter data corresponding to those described above for the transmission data can also be determined.

Figure 18:
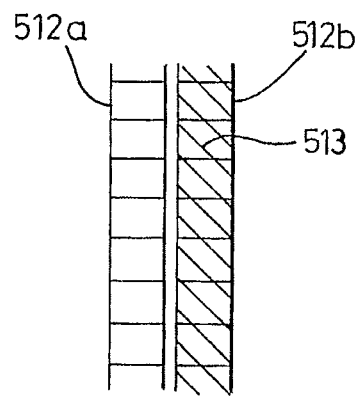
FIG. 18 is a partial view of a dual energy scanner according to a further embodiment of the invention.

Referring to FIG. 18, in a further embodiment of the invention the transmission detectors 512 that are used to generate the tomographic image data are arranged to measure the X-ray transmission over different energy ranges. This is achieved by having two sets of detectors 512a, 512b, each forming a ring around the conveyor. The two sets are at different axial locations along the direction of travel of the conveyor, in this case being adjacent to each other in the axial direction. The first set 512a has no filter in front of it, but the second set 512b has a metal filter 513 placed between it and the X-ray source 510. The first set of detectors 512a therefore detects transmitted X-rays over a broad energy range, and the second set 512b detects X-rays only in a narrower part of that range at the high energy end.

As the item to be scanned moves along the conveyor, each thin volume or slice of it can be scanned once using the first set of detectors 512a and then scanned again using the second set 512b. In the embodiment shown, the same source 510 is used to scan two adjacent volumes simultaneously, with data for each of them being collected by a respective one of the detector sets 512a, 512b. After a volume of the item has moved past both sets of detectors and scanned twice, two sets of image data can be formed using the two different X-ray energy ranges, each image including transmission (and hence attenuation) data for each pixel of the image. The two sets of image data can be combined by subtracting that for the second detector set 512a from that of the first 512b, resulting in corresponding image data for the low energy X-ray component.

The X-ray transmission data for each individual energy range, and the difference between the data for two different ranges, such as the high energy and low energy, can be recorded for each pixel of the image. The data can then be used to improve the accuracy of the CT images. It can also be used as a further parameter in the threat detection algorithm.

Figure 19:
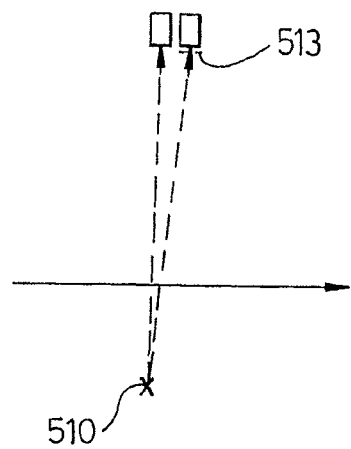
FIG. 19 is a further partial view of the scanner of FIG. 18.

It will be appreciated that other methods can be used to obtain transmission data for different ranges of X-ray energies. In a modification to the system of FIGS. 18 and 19, balanced filters can be used on the two detector sets. The filters are selected such that there is a narrow window of energies that is passed by both of them. The image data for the two sets of detectors can then be combined to obtain transmission data for the narrow energy window. This enables chemical specific imaging to be obtained. For example it is possible to create bone specific images by using filters balanced around the calcium K-edge energy. Clearly this chemical specific data can be used effectively in a threat detection algorithm.

In a further embodiment, rather than using separate filters, two sets of detectors are used that are sensitive to different energy X-rays. In this case stacked detectors are used, comprising a thin front detector that is sensitive to low energy X-rays but allows higher energy X-rays to pass through it, and a thick back detector sensitive to the high energy X-rays that pass through the front detector. Again the attenuation data for the different energy ranges can be used to provide energy specific image data.

In a further embodiment two scans are taken of each slice of the object with two different X-ray beam energies, achieved by using different tube voltages in the X-ray source, for example 160 kV and 100 kV. The different energies result in X-ray energy spectra that are shifted relative to each other. As the spectra are relatively flat over part of the energy range, the spectra will be similar over much of the range. However, part of the spectrum will change significantly. Therefore comparing images for the two tube voltages can be used to identify parts of the object where the attenuation changes significantly between the two images. This therefore identifies areas of the image that have high attenuation in the narrow part of the spectrum that changes between the images. This is therefore an alternative way of obtaining energy specific attenuation data for each of the sub-volumes within the scanned volume.

Figure 20:
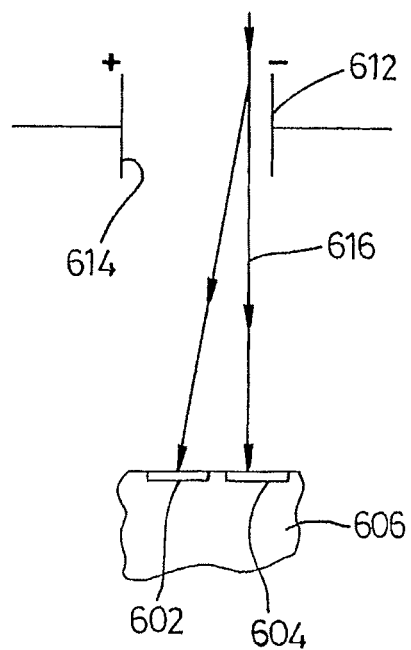
FIG. 20 is a schematic view of a dual energy X-ray source of a further embodiment of the invention.

Referring to FIG. 20 in a further embodiment of the invention, two different X-ray energy spectra are produced by providing an anode 600 in the X-ray tube that has target areas 602, 604 of two different materials. In this case, for example, the anode comprises a copper base 606 with one target area 602 of tungsten and one 604 of uranium. The electron source 610 has a number of source points 612 that can be activated individually. A pair of electrodes 612, 614 is provided on opposite sides of the path of the electron beam 616 which can be controlled to switch an electric field on and off to control the path of the electron beam so that it strikes either one or the other of the target areas 602, 604. The energy spectrum of the X-rays produced at the anode will vary depending on which of the target areas is struck by the electron beam 616.

This embodiment uses an X-ray source similar to that of FIG. 1a, with the different target areas formed as parallel strips extending along the anode 27. For each active electron source point two different X-ray spectra can be produced depending on which target material is used. The source can be arranged to switch between the two target areas for each electron source point while it is active. Alternatively the scan along the anode 27 can be performed twice, once for one target material and once for the other. In either case further electron beam focusing wires may be needed to ensure that only one or the other of the target materials is irradiated by the electron beam at one time.

Depending on the angle at which the X-ray beam is extracted from the anode, the beams from the two target areas 602, 604 can in some cases be arranged to pass though the same imaging volume and be detected by a common detector array. Alternatively they may be arranged to pass through adjacent slices of the imaging volume and detected by separate detector arrays. In this case the parts of the imaged item can be scanned twice as the item passes along the conveyor in a similar manner to the arrangement of FIG. 18.

Figures 21, 22:
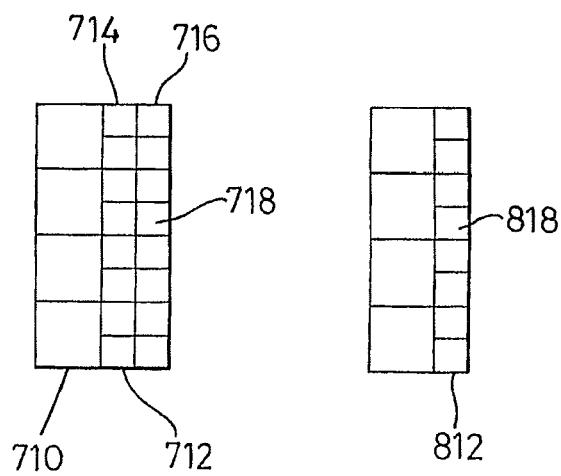
FIG. 21 is a schematic view of a detector array of a scanner according to a further embodiment of the invention.
FIG. 22 is a schematic view of a detector array of a scanner according to a further embodiment of the invention.

Referring to FIG. 21, in a further embodiment, two detector arrays are provided in a single scanner, adjacent to each other in the axial direction, one 710 corresponding to that of FIG. 1 and being arranged to form a RTT image, and the other, 712, being of a higher resolution, and being arranged to produce a high resolution projection image of the scanned object. In this embodiment the high resolution detector array 712 comprises two parallel linear arrays 714, 716 each arranged to detect X-rays at a different energy, so that a dual energy projection image can be produced. In the embodiment of FIG. 22, the high resolution array 812 comprises two stacked arrays, a thin array on top arranged to detect lower energy X-rays but transparent to higher energy X-rays, and a thicker array beneath arranged to detect higher energy X-rays. In both cases, the two detector arrays are arranged close enough together in the axial direction to be able to detect X-rays from a single linear array of source points.

Figure 23:
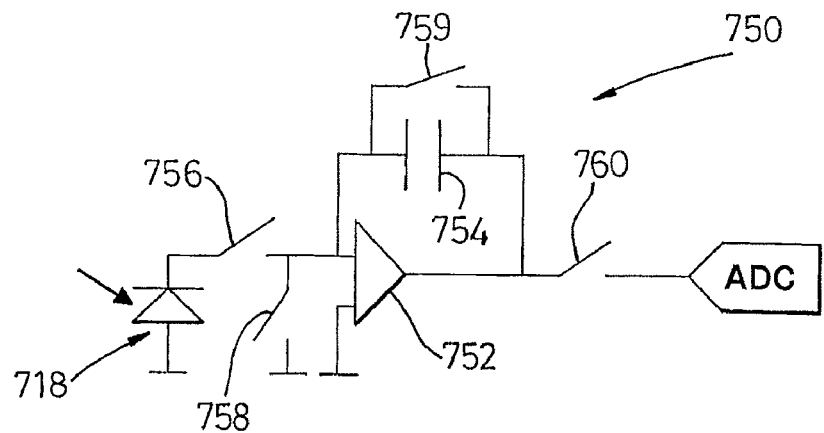
FIG. 23 is a circuit diagram of a data acquisition circuit of the embodiment of FIG. 21.

In order to provide a projection image, data needs to be captured from all of the detectors in the high resolution array 712, 812 when only one source point is active. Referring to FIG. 23, in order to do this each detector 718, 818 in the high resolution array is connected to an integrator 750. The integrator comprises an amplifier 752 in parallel with a capacitor 754. An input switch 756 is provided between the detector 718 and the amplifier 752, a reset switch 758 is provided across the input terminals of the amplifier, and a further reset switch 759 connected across the capacitor 754, and a multiplexing switch 760 is provided between the integrator and an analogue to digital converter ADC.

In operation, while the detector 718 is not required to be active, all of the switches except for the multiplexing switch 760 are closed. This ensures that the capacitor 754 is uncharged and remains so. Then, at the start of the period when the detector is required to gather data, the two reset switches 758, 759 are closed so that any X-rays detected by the detector 718 will cause an increase in the charge on the capacitor 754, which results in integration of the signal from the detector 718. When the period for data collection has ended, the input switch 756 is opened, so that the capacitor will remain charged. Then, in order for the integrated signal to be read from the integrator, the output switch 760 is closed to connect the integrator to the ADC. This provides an analogue signal to the ADC determined by the level of charge on the capacitor 754, and therefore indicative of the number of X-rays that have been detected by the detector 718 during the period for which it was connected to the integrator. The ADC then converts this analogue signal to a digital signal for input to the data acquisition system. To produce a single projection image, all of the high resolution detectors are used to collect data at the same time, when one of the X-ray source points is active.

Figure 24:
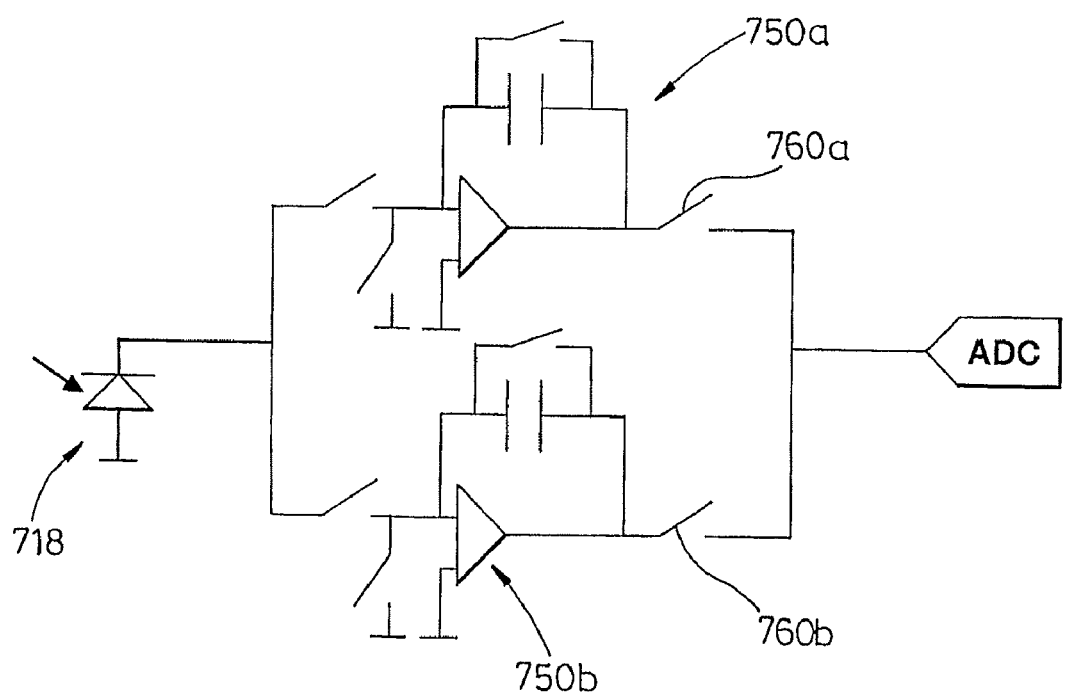
FIG. 24 is a circuit diagram of a data acquisition circuit of a further embodiment of the invention.

Referring to FIG. 24, in a further embodiment, each detector 718 is connected to two integrators 750a, 750b in parallel, each of which is identical to that of FIG. 23. The outputs from the two integrators are connected via their output switches 760a, 760b to an ADC. This enables each integrator to be arranged to integrate the signal from the detector 718 at a different point in the scan of the X-ray source, and therefore to collect data for a separate image, the two images being from different angles with different X-ray source points. For example this can be used to produce projection images from orthogonal directions which can be used to build up a high resolution 3-dimensional image, from which the position of features in the imaged package can be determined in three dimensions.

The high resolution image can be useful when combined with the RTT image, as it can help identify items for which higher resolution is needed, such as fine wires.

The invention claimed is:

1. An X-ray scanning system for scanning an object comprising at least one X-ray source arranged to generate X-rays from a plurality of X-ray source positions around a scanning region wherein said X-ray sources do not move relative to said object during a scan, a first set of detectors arranged to detect X-rays transmitted through the scanning region wherein said first set of detectors is configured in a circular array defined by a first radius and wherein said circular array is positioned opposite said at least one X-ray source with an inspection volume defined therebetween, a second set of detectors arranged to detect X-rays scattered within the scanning region wherein the second set of detectors is arranged in at least one circular array having said first radius, wherein said circular array is positioned axially adjacent to said at least one X-ray source and on the same side of the inspection volume, wherein a collimator is positioned in front of the second set of detectors to collimate the X-rays scattered toward each of said second set of detectors, and wherein the collimator defines a receiving direction that is inclined relative to a plane defined by the detectors, and processing means arranged to process outputs from the first set of detectors to generate CT image data which defines an image of the scanning region, to analyze the CT image data to identify an object within the image, and to process the outputs from the second set of detectors to generate scattering data, and to associate parts of the scattering data with the object.

2. A system according to claim 1 wherein the processing means is arranged to determine from the scattering data a measure of the level of scattering from different positions within the scanning region.

3. A system according to claim 2 wherein the scattering is coherent scattering.

4. A system according to claim 3 wherein the processing means is arranged to determine, from the position of the detector that detects a scattered X-ray and the direction from which the X-ray was directed at the scanning region, the position at which the X-ray was scattered.

5. A system according to claim 1 wherein the scattering is incoherent scattering.

6. A system according to claim 1 wherein the processing means is arranged to determine from the CT image data an indication of a position at which the scattered X-rays may have been scattered.

7. A system according to claim 1 wherein the processing means is arranged define a plurality of pixels within the image, and to identify at least one of the pixels as being associated with the object, and to associate parts of the scattering data with respective pixels.

8. A system according to claim 1 wherein the two sets of detectors are on opposite sides of the source.

9. A system according to claim 1 wherein the first set of detectors are arranged in an arc defining an axis of the system.

10. A system according to claim 9 wherein the second set of detectors are arranged in a plurality of arcs around the system axis, the arcs being spaced along the axis.

11. A system according to claim 1 further comprising a data collecting system for collecting said scattering data and said CT image, wherein said data collecting system comprises a memory having a plurality of areas each being associated with a respective area of said image, data input means arranged to receive input data from a plurality of X-ray detectors in a predetermined sequence, at least one processor arranged to generate from the input data CT image data and scattering data associated with each of the areas of the image, and to store the CT image data and the scattering data in the appropriate memory areas.

12. A system according to claim 11 wherein the processor is arranged to determine which area any part of the CT image data or scattering data is to be associated with at least partly on the basis of which detector it is received from.

13. A system according to claim 11 wherein the processor is arranged to determine which area any part of the CT image data or scattering data is to be associated with, at least partly on the basis of the position at which the X-ray was produced.

14. A system according to claim 11 further comprising a look-up table having entries stored therein that associate each of the detectors with a respective area of the image.

15. A system according to claim 11 wherein the processor is arranged to store CT image and scattering data in the memory for each of a plurality of tomographic scans of an object as the object moves through an imaging region, and to extract the CT image data from the memory after each of the scans so that CT image data for a subsequent scan can be stored in the memory.

16. An X-ray imaging system according to claim 15 wherein the processor is arranged to combine the CT image data from the tomographic scans to produce a three-dimensional image of the object.

\* \* \* \* \*